(12) United States Patent
Kim et al.

(10) Patent No.: US 8,043,827 B2
(45) Date of Patent: Oct. 25, 2011

(54) SINGLE MOLECULE-FORMAT REAL-TIME BIOLUMINESCENCE IMAGING PROBE

(75) Inventors: Sung-Bae Kim, Ibaraki (JP); Hiroaki Tao, Ibaraki (JP); Moritoshi Sato, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 200 days.

(21) Appl. No.: 12/343,830

(22) Filed: Dec. 24, 2008

(65) Prior Publication Data
US 2009/0176239 A1    Jul. 9, 2009

(30) Foreign Application Priority Data

Dec. 25, 2007  (JP) ................................ 2007-332253

(51) Int. Cl.
*C12Q 1/66* (2006.01)
*C12Q 1/68* (2006.01)
*C12N 9/02* (2006.01)
*C12N 15/00* (2006.01)
*C12P 21/06* (2006.01)
*C07H 21/04* (2006.01)

(52) U.S. Cl. ............... 435/8; 435/6; 435/189; 435/69.1; 435/320.1; 536/23.4; 536/23.1

(58) Field of Classification Search .................. 435/8, 6, 435/189, 69.1, 320.1; 536/23.4, 23.1
See application file for complete search history.

(56) References Cited

U.S. PATENT DOCUMENTS

2009/0269781 A1* 10/2009 Kim et al. ...................... 435/7.1
2010/0273150 A1* 10/2010 Umezawa et al. ................ 435/6

FOREIGN PATENT DOCUMENTS

WO    WO 2007/120522 A2 * 10/2007

OTHER PUBLICATIONS

Kim et al., Integrated molecule-format bioluminescent probe for visualizing androgenecity of ligands based on intramolecular association of androgen receptor with its recognition peptide. Anal. Chem., 2007, vol. 79 (5): 1874-1880.*
Kim et al., Bioluminescent indicator for determining protein-protein interactions using intramolecular complementation of split click beetle luciferase. Anal. Chem., 2007, vol. 79 (13): 4820-4826.*
Miyawaki et al., Fluorescent indicators for Ca2+ based on green flourescent proteins and calmodulin. Nature, 1997, vol. 388: 882-887.*
Romoser et al., Detection in living cells Ca2+-dependent changes in fluorescence emission of an indicator composed of two green fluorescent protein variants linked by a calmodulin-binding sequence. J. Biol. Chem., 1997, vol. 272 (20): 13270-13274.*
Teruel et al., Differential codes for free Ca2+-calmodulin signals in nucleus and cytosol. Current Biology, 2000, vol. 10: 86-94.*
Cameron ER., Recent advances in transgenic technology. 1997, vol. 7: 253-265.*
Kappel et al., Regulating gene expression in transgenic animals. Current Opinion in Biotechnology 1992, vol. 3: 548-553.*
Mullins et al., Transgenesis in nonmurine species. Hypertension, 1993, vol. 22 (4): 630-633.*
Mullins et al., Transgenesis in the rat and larger mammals. J. Clin. Invest., 1996, vol. 97 (7): 1557-1560.*
Wigley et al., Site-specific transgene insertion: an approach. Reprod. Fert. Dev., 1994, vol. 6: 585-588.*
Remy et al., A highly sensitive proetin-proetin interaction assay based on *Gaussia luciferase*. Nature Methods., 2006, vol. 3 (12): 977-979.*
Venisnik et al., Fusion of *Gaussia luciferase* to an engineered anti-carcinoembryonic antigen (CEA) antibody for in vivo optical imaging. Mol Imaging Biol., 2007, vol. 9 : 267-277.*

* cited by examiner

*Primary Examiner* — Ganapathirama Raghu
(74) *Attorney, Agent, or Firm* — Westerman, Hattori, Daniels & Adrian, LLP

(57) ABSTRACT

The present invention provides an "in vivo and in vitro real-time bioluminescence imaging means," which can transmit a detection signal promptly in response to an external signal, while taking advantage of a single-molecule-format luminescent probe as a bioluminescent means.

The present invention is characterized by using, as a single-molecule-format luminescent probe utilizing the increase and decrease of a second messenger level as an index, a fusion protein including a single-chain protein containing a second messenger recognition protein and optionally a peptide which is capable of binding with the protein, and linked respectively to the N-terminus and the C-terminus thereto, an N-terminal fragment (N-LE) and a C-terminal fragment (C-LE) generated by dissecting a luminescent enzyme (LE). A single-molecule-format luminescent probe could be provided, which makes it possible to observe light emission (extinction) in vivo as well as in vitro, as a result of a conformational change of the second messenger recognition protein induced by the binding (unbinding) with a second messenger, and the subsequent association or dissociation between the N-LE and the C-LE flanked at both termini of the recognition protein.

22 Claims, 10 Drawing Sheets

[FIG 1]
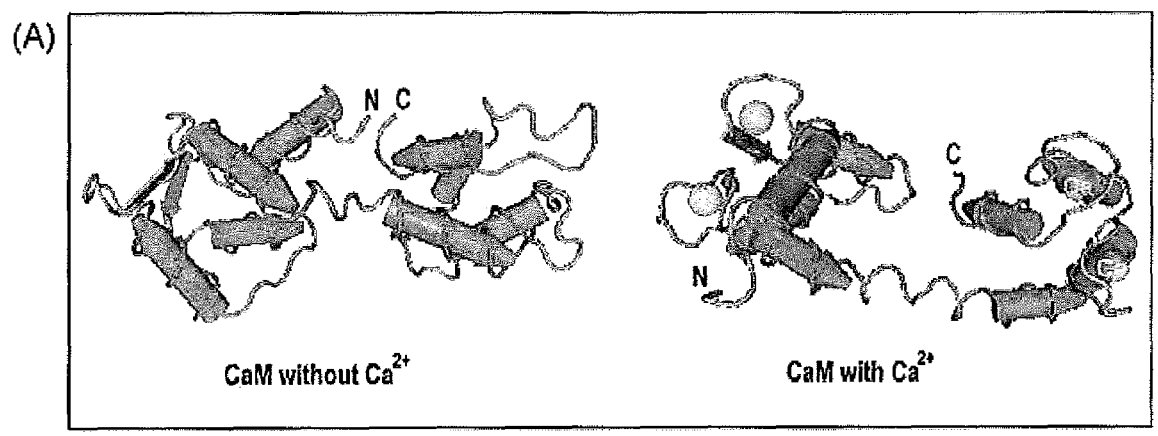
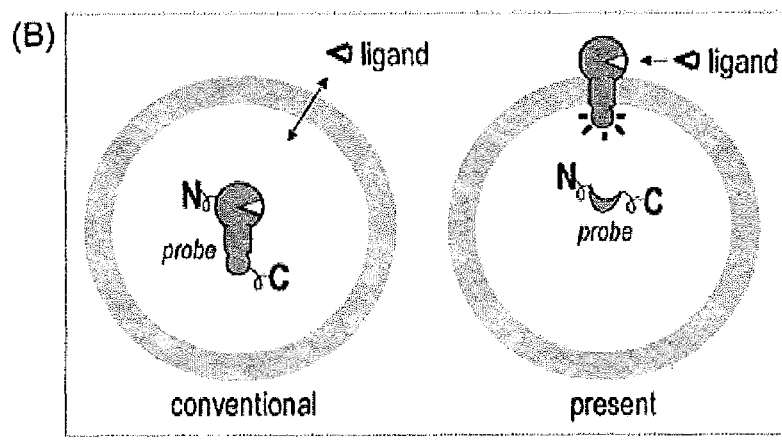

[FIG 2]
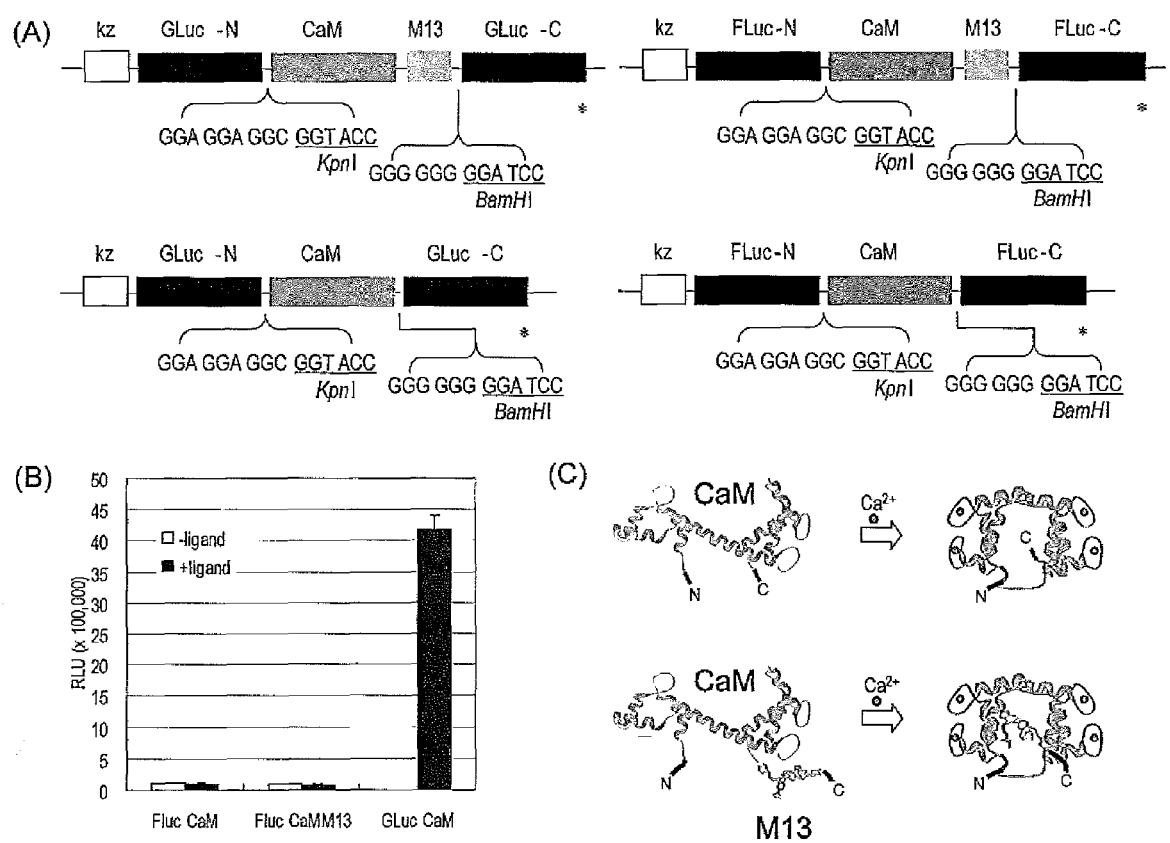

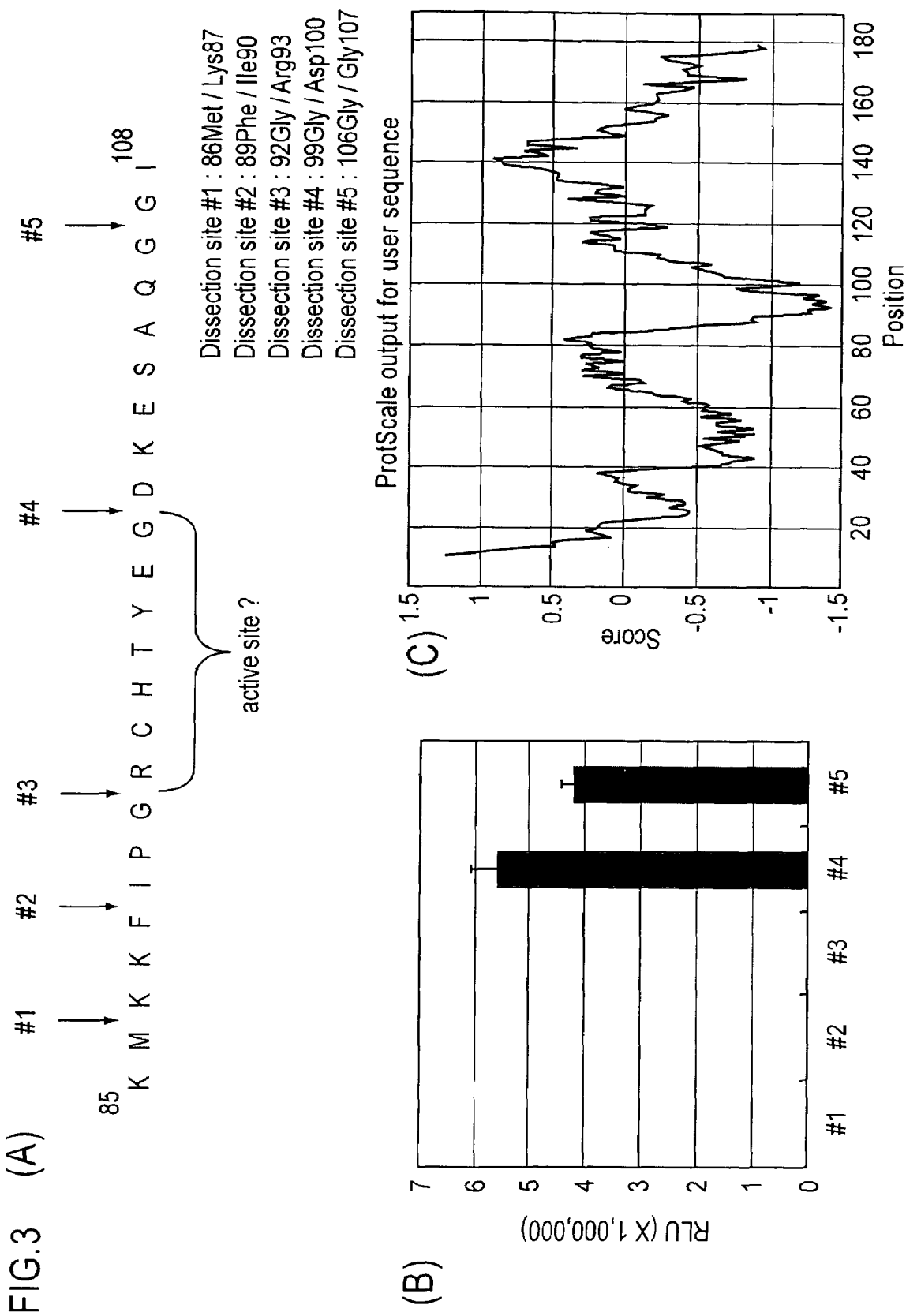

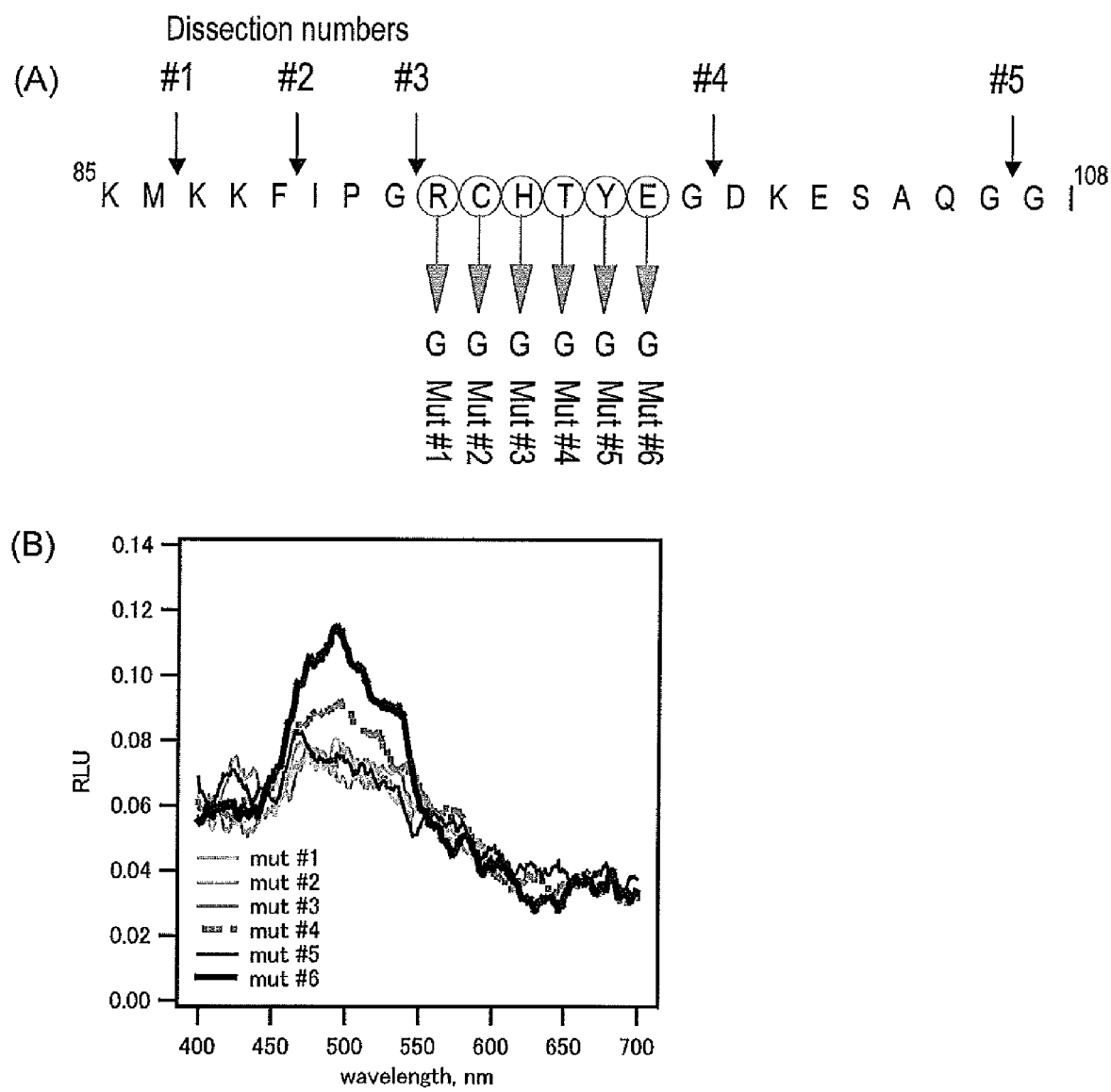
[FIG 4]

FIG. 5
(A)
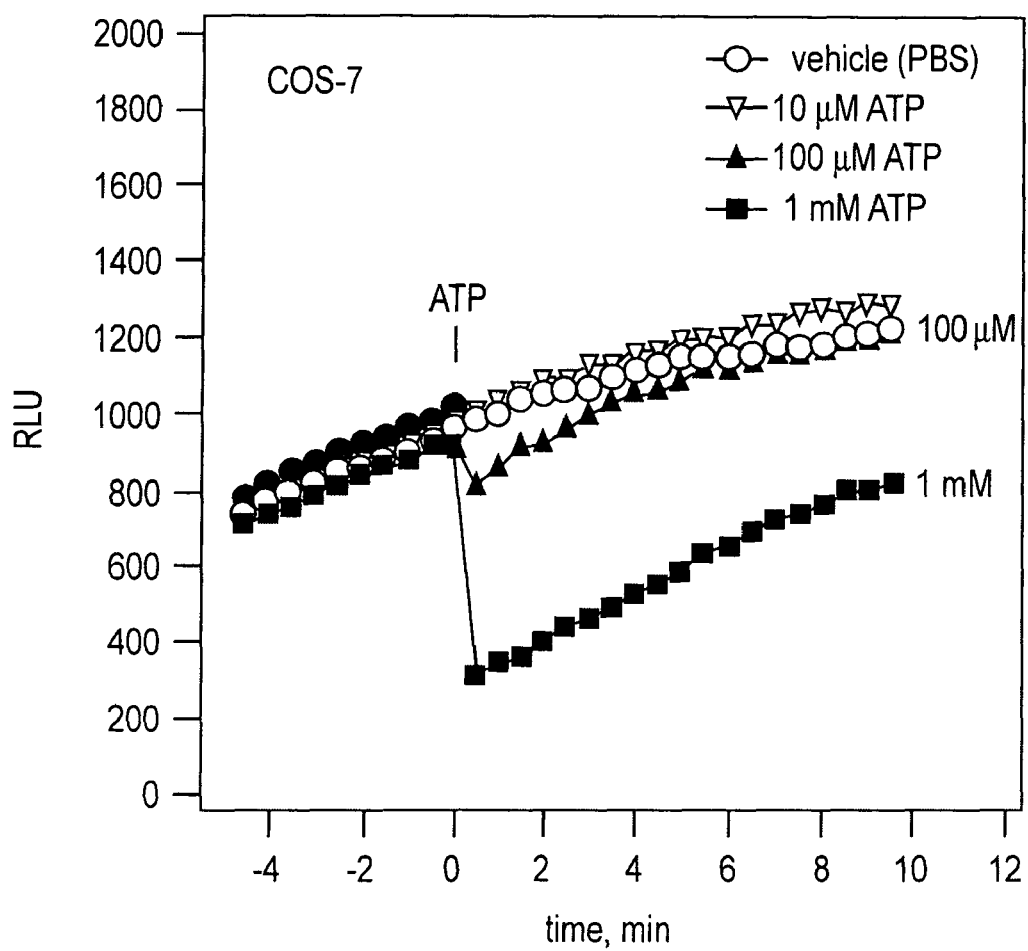
(B)
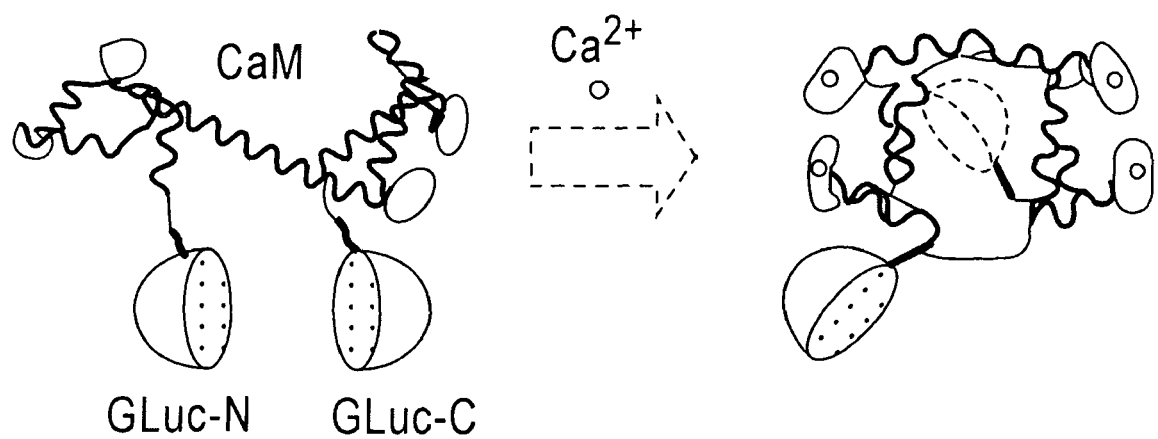

[FIG 6]
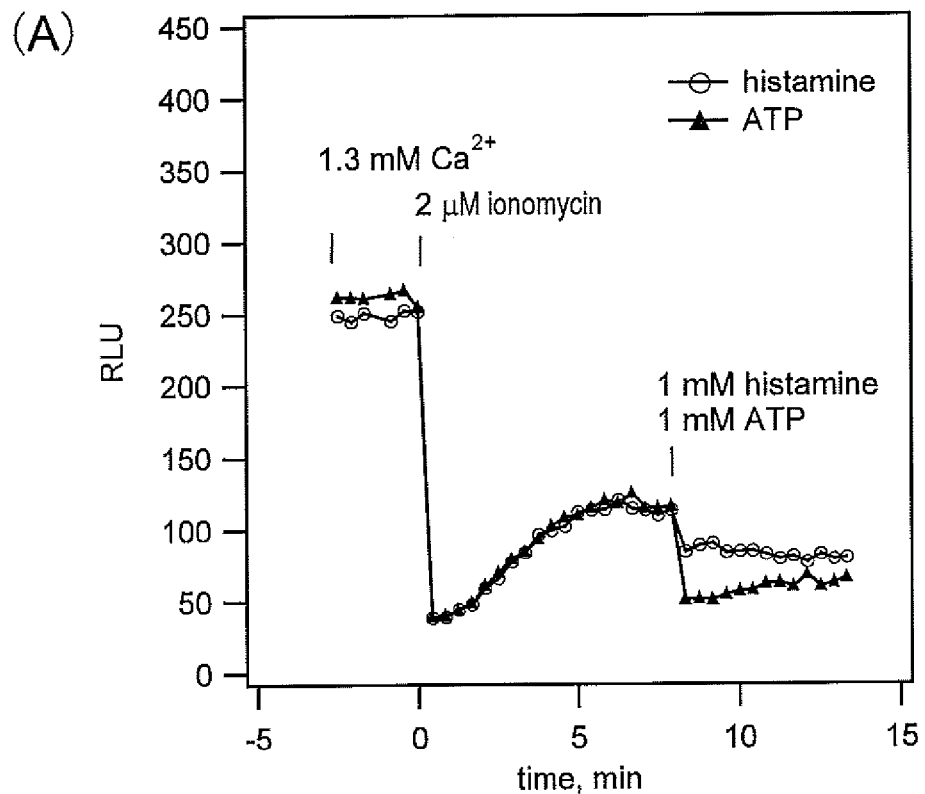
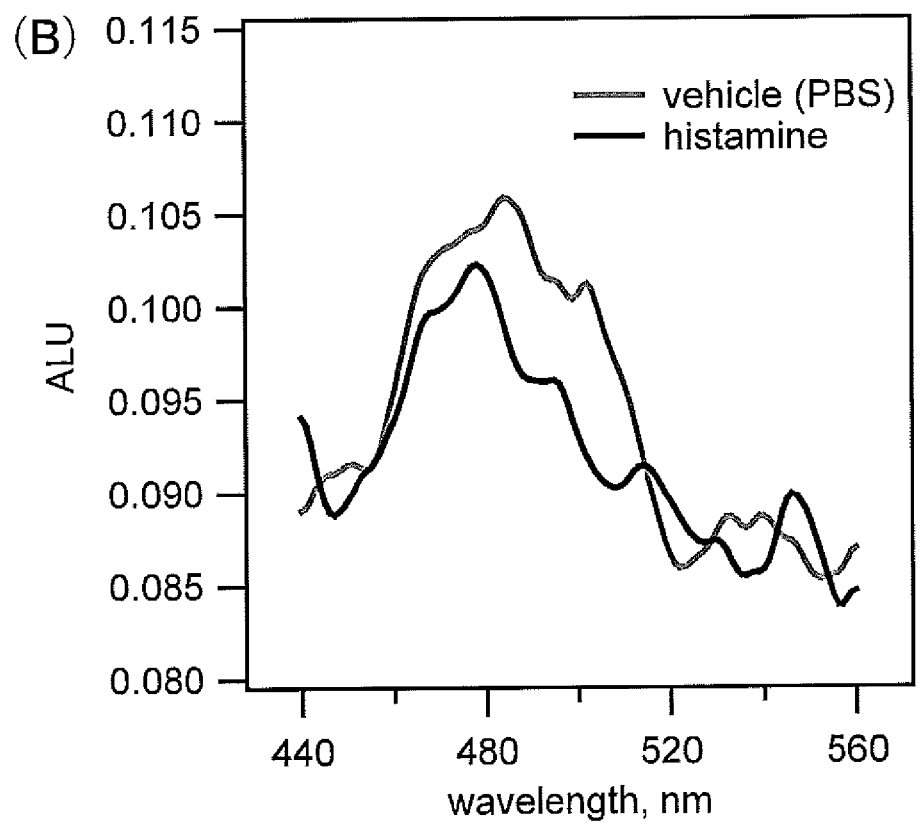

[FIG 7]
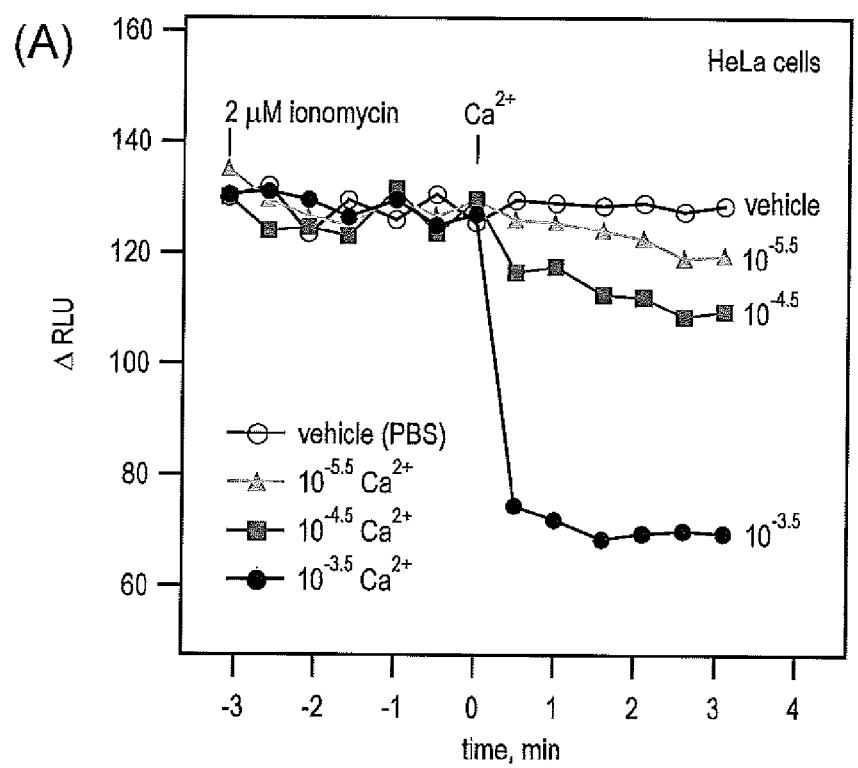
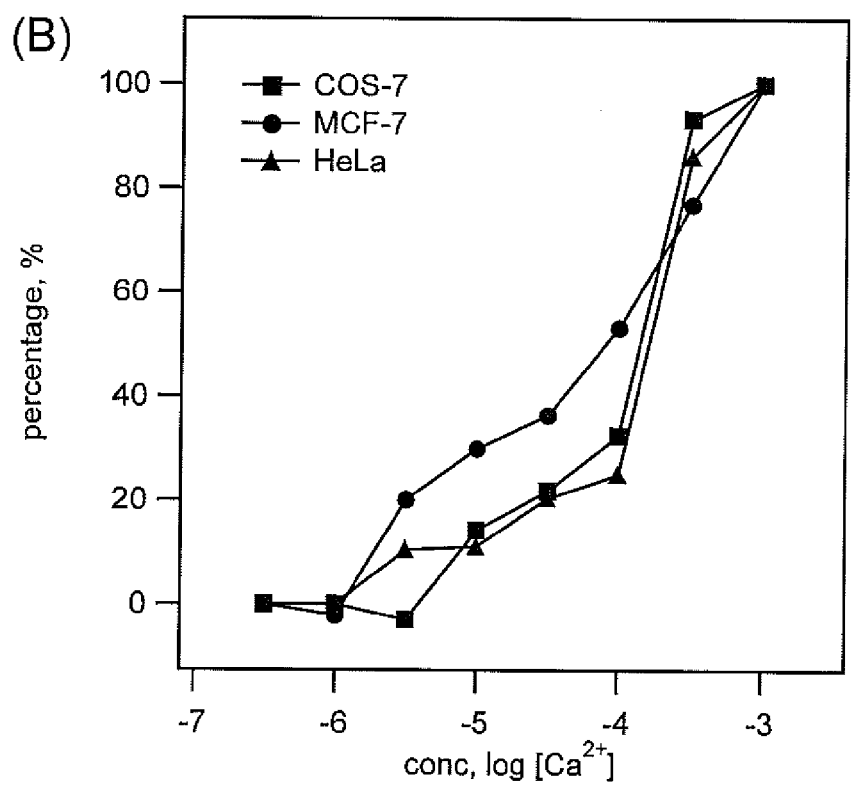

FIG. 9
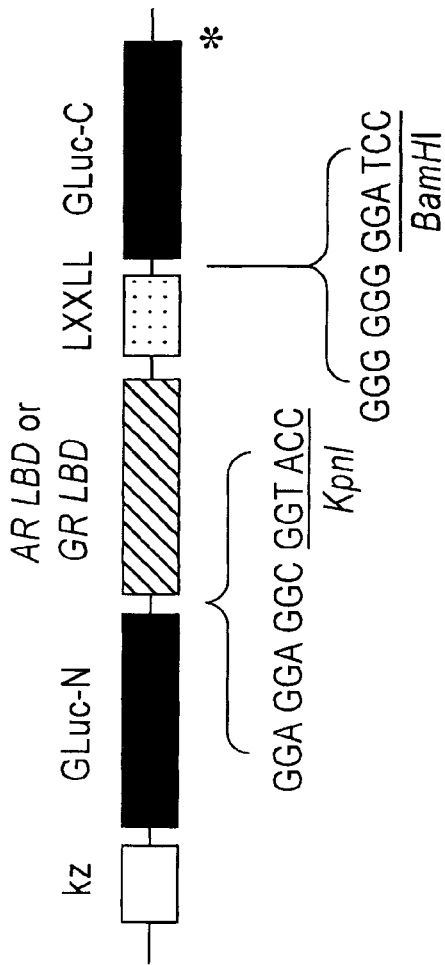
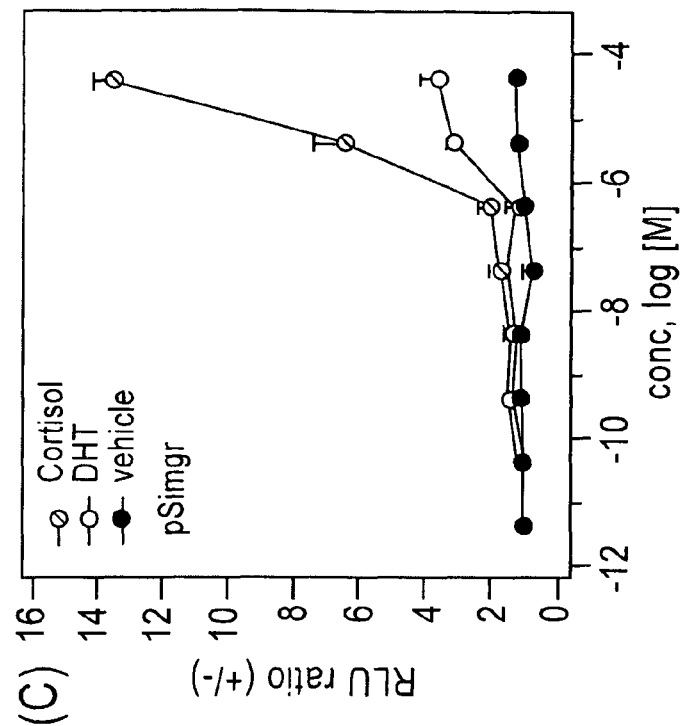
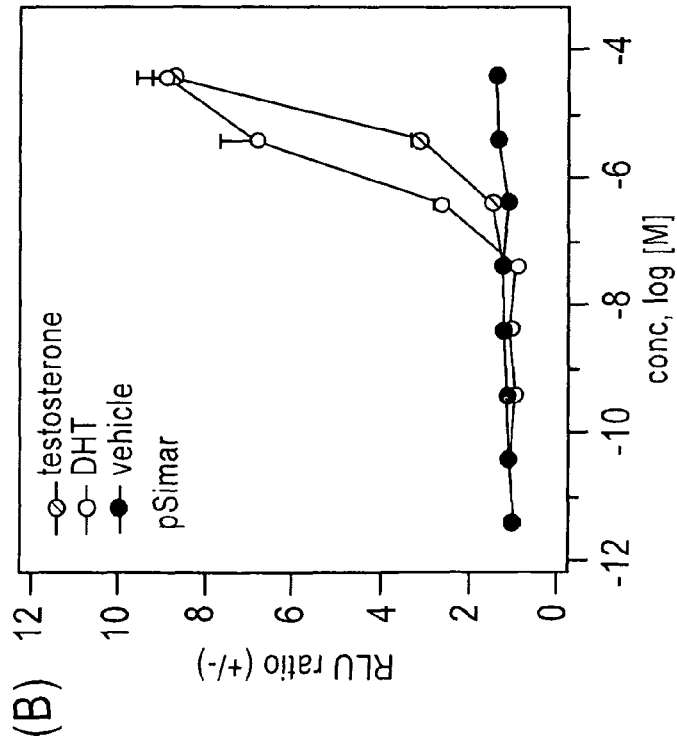

[FIG 10]
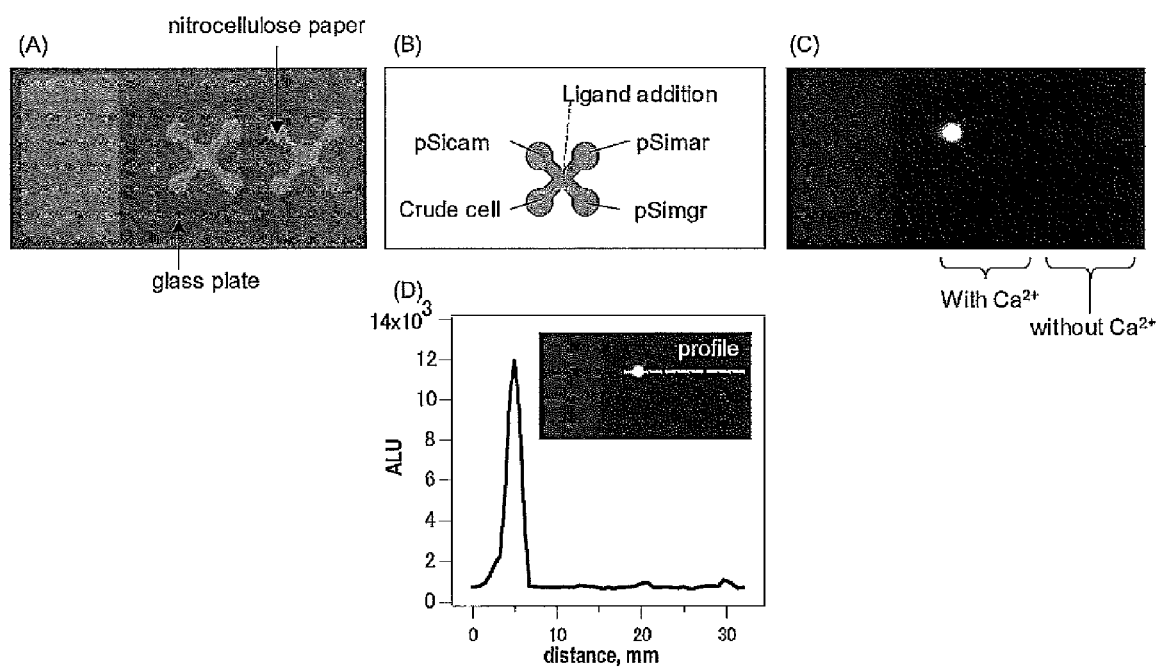

SINGLE MOLECULE-FORMAT REAL-TIME BIOLUMINESCENCE IMAGING PROBE

TECHNICAL FIELD

The present invention relates to a fusion protein useful as a real-time luminescence imaging probe, which utilizes a conformational change of a second messenger recognition protein induced by its association or dissociation with a second messenger. The present invention also relates to a fusion protein useful as a versatile single-chain luminescent probe utilizing a Gaussia luciferase bisected at an optimal position.

BACKGROUND ART

The realm of nature in which we are dwelling is inhabited by innumerable higher and lower organisms, and these organisms are maintaining their life phenomena on the basis of common molecular mechanisms such as expression of proteins by means of DNAs in response to external stimuli.

In both eukaryotic cells and prokaryotic cells, rapidly responding to the temperature, signal transducers, the presence or absence of nutrients, and the like in the breeding environment is directly related to the matter of life and death of the organism. Therefore, in regard to nutrition, energy control, propagation, and signal transduction of sensory organs such as in visual and auditory senses, living cells completes relevant signal transduction in the time ranging from a few milliseconds to minutes.

Various techniques have been developed hitherto as the means to examine such life phenomena, and some of them have already been commercialized. In recent studies conducted in a wide range of life science fields, molecular imaging within individual cells and animals has become the main trend of research for certain life phenomena (Massoud, T. F. and Gambhir, S. S. Genes & Development, 2003, 17, 545-580). In particular, research and development on bioanalysis utilizing fluorescent dye proteins such as green fluorescent protein (GFP), is becoming popular, and a technology of visualizing protein-protein interactions, or degrees of activity of proteins in a signal transduction system, particularly using fluorescence resonance energy transfer (FRET; a phenomenon in which between two fluorescent molecules, the excitation energy of one fluorescent molecule is transferred to the other fluorescent molecule to emit fluorescence), namely, so-called imaging technology is on the focus of interest. On the other hand, a molecular imaging technology utilizing lighting enzymes (LE) such as firefly luciferase (FLuc) is also attracting high attention over the world, and the research and development thereof is in intense competition.

These molecular imaging techniques may be classified by the approximate signal transduction time taken from the in vivo generation of signals to the measurement of the signals, as follows.

The molecular imaging technique requiring the longest time may be exemplified by a reporter gene assay. In this assay, the intensity, property and the like of the initial exogenous stimulators can be determined, on the basis of the intensity of luminescence or fluorescence of a reporter protein which is expressed as a result of the activation of transcription factors by exogenous stimulators, or the like, as an index. This technique requires 24 hours on the average until the amount of the reporter protein is sufficiently accumulated. This technique has been widely used in the investigation of the activity of a steroid or a chemical substance.

As a molecular imaging technique requiring the second longest time, a technique based on protein splicing was introduced (Kim, S. B., Ozawa, T., Watanabe, S., Umezawa, Y. Proc. Natl. Acad. Sci. U.S.A., 2004, 101, 11542-11547). Protein splicing means a self-catalytic splicing reaction occurring between a certain protein sequence and another protein sequence. A protein which will serve as a reporter, is bisected (N-terminal side and C-terminal side) beforehand, and the bisected fragments are respectively linked to both termini of a splicing protein. And then, the fragments may be spliced to restore a full reporter protein in response to an appropriate exogenous stimulator. The resulting recovery of luminescence or fluorescence intensities were taken as an index of the intensity of the initial external stimulator. This technique requires 2 hours at the lower limit, since sufficient time is needed for the reaction between the two fragmentized protein fragments. This technique is being effectively used for imaging the intracellular trafficking of proteins, and the like.

As a molecular imaging technique requiring the third longest time, a protein self-complementation method may be mentioned. This technique makes use of an increment of the intensity of luminescence or fluorescence generated when bisected fragments of a reporter protein are approximated to recover the activity, as the signal for analysis. For instance, in order to investigate the presence or absence of certain target protein-protein interaction, the target proteins are each linked with one of the bisected fragments of a reporter protein. Later, the reporter protein fragments are sufficiently approximated only when the two target proteins interact in response to an exogenous signal. The intensity of luminescence or fluorescence of the reconstituted reporter protein triggered by the binding between the two aimed proteins as a result is taken as an index, to evaluate the intensity of the original external signal (two-molecule-format probe: WO 2002/008766, WO 2004/104222, and Kim, S. B., Awais, M., Sato, M., Umezawa, Y., and Tao, H. Anal. Chem. 2007, 79, 1874-1880). This technique is used to evaluate the activity of a steroid or a chemical substance, and thus requires a measurement time of about 20 minutes after steroid stimulation. Recently, the inventors of the present invention have developed a method of bioimaging an intramoleculer protein-protein interaction inside a single molecule, based on the principle of self-complementation of a LE, and filed a patent application on the method (Japanese Patent Application No. 2007-005144). The feature of this technique is to integrate all the components for ligand-sensing and light emission in a single molecule, and thus enable to detect a conformation change of the ligand recognition protein induced by a ligand as one-dimensional luminescence intensity mode. Moreover, as an advanced form of the previous technique, the inventors of the present invention have further developed a technique for discriminating multiple activities of a single ligand in respectively different colors (green and red), and filed a patent application on the technique (Japanese Patent Application No. 2007-202308).

As a molecular imaging method which can be performed in a time shorter than this, there is a method based on fluorescence resonance energy transfer (FRET). In this technique, the fluorescence energy transfer occurring between two fluorescent dye proteins in proximity can be used as an index to measure the degree of the interaction between the two proteins (JP-A No. 2002-017359 and JP-A No. 2007-49943). The inventors of the present invention suggest a probe capable of visualizing the binding of cGMP with its target molecule (cGMP-binding protein) based on the FRET phenomenon (JP-A No. 2002-017359), or a probe capable of similarly visualizing IP3 using the FRET phenomenon (JP-A No. 2007-49943). This technique can achieve fluorescence imaging of the molecular phenomena in a single cell on a real-time basis. This technique provides the fastest imaging means among those that have been developed thus far.

The probes for detecting target ligands using the FRET phenomenon (JP-ANo. 2002-017359, JP-ANO. 2007-49943, JP-A NO. 2004-325253, Awais, M.; Sato, M.; Lee, X. F.; Umezawa, Y. Angew. Chem. Int. Ed. 2006, 45, 2707-2712, and Schaufele, F.; Carbonell, X.; Guerbadot, M.; Borngraeber, S.; Chapman, M. S.; Ma, A. A.; Miner, J. N.; Diamond, M. I. Proc. Natl. Acad. Sci. U.S.A. 2005, 102, 9802-9807) are excellent in that, as described above, they are capable of detecting ligands in short times, and also capable of detecting agonists and antagonists each distinctively. However, the fluorescent probes have high background fluorescence due to autofluorescence, and require a high sensitivity fluorescence microscope, a precision filtering apparatus and a trained technician to measure the energy transfer of two chromophores with high precision. Also, since excitation by short wavelength light from an external source is required, it has been very difficult to perform bioanalysis in living subjects where the absorption of short wavelength light is significant.

In addition to the above-described technologies, synthetic fluorescent dye reagents such as Fura and Indo-1, have been introduced to employ intracellular molecular imaging (Schlegel, S., Steen, M., Guse, A. H. Mol. MED. 2006, 12, S23-S23 (Suppl. 1)), but these synthetic substances have problems in that they cause cytotoxicity, accumulation in some parts of cells, and lack selectivity to target ligands.

On the other hand, bioluminescence imaging is advantageous compared with fluorescence, in that:

(1) the background emission is low;
(2) no excitation by an external light is required;
(3) the apparatus is very simple, compact, and easy to be miniaturized;
(4) the emission light has excellent tissue permeability and thus is appropriate for in vivo imaging; and the like.

For this reason, the inventors of the present invention have put an effort in developing a molecular imaging probe utilizing bioluminescence. In the case of the conventional detection method for protein-protein interaction based on protein splicing or self-complementation, which method utilizes the restorability of a partitioned reporter molecule (WO 2002/008766, WO2004/104222, and Kim, S. B., Ozawa, T., Watanabe, S., Umezawa, Y. Proc. Natl. Acad. Sci. U.S.A., 2004, 101, 11542-11547), since the respective split reporter molecules are introduced into the cells as separate probe components (two-molecule-format probe), there occurs an improper stoichiometry because the respective expression levels of the probe components differ from each other. It was also strongly feared that such stoichiometric variance causes inefficiency of the probe in sensing a ligand.

Therefore, the inventors of the present invention recently developed a single-molecule-format luminescent probe comprising excellent analytical performance, in which all of the elements necessary for the ligand sensing and light emission are integrated in a single molecule (Japanese Patent Application Nos. 2007-202308 and 2007-005144). However, the probe takes approximately 10 minutes to 20 minutes from the recognition of a ligand to the light emission. The large molecular weight (92 kD) of the conventional probes imposes a burden on the cells, and thus is not adequate to trace the molecular phenomena which take short time, in the living cells.

That is, in the case of conventional bioluminescence imaging probes, no matter whether a single-molecule-format or a two-molecule-format, the molecular weights of the probes are ever heavy because a ligand recognition domain inherent to a ligand-specific receptor is simply incorporated into the probe, and luminescent enzymes with a heavy molecular weight have been used. Furthermore, the target ligand must permeate the cell membrane and reach the probe in the cytoplasm, but in the case of insulin, various growth hormones, cytokines and the like, since these molecules originally cannot permeate the cell membrane, they cannot be detected with conventional probes expressed within the cells. Even in the case of ligands which are capable of permeating the cell membrane, since the step of membrane permeation is the rate-limiting step, thus requiring a measurement time of about several ten minutes, the real time observation of various life phenomena in a cell cannot be made by any conventional means.

In order to observe life phenomena in a living cell on a real-time basis, it is most effective to carry out molecular imaging of the signal transduction of second messengers inside the living cell, and a large number of analytic technologies have been developed and proposed in relation to the molecular imaging of second messengers (particularly, calcium ions) (JP-A No. 2007-49943 and Miyawaki A., Llopsis J., Heim R., McCaffery J. M., Adams J. A., Ikura M., Tsien R. Y. Nature, 1997, 388 (6645), 882-887).

In particular, a calcium sensor emitting fluorescence based on the above-discussed principle of FRET, and includes a protein containing calmodulin, which is a calcium recognition protein, and a peptide capable of binding to calcium ion-bound calmodulin (M13), genetic mutants of GFP such as cyan fluorescent protein (CFP), yellow fluorescent protein (YFP) linked to the two termini of calmodulin, as well as probes ameliorated therefrom are widely used as probes which can detect calcium ions serving as a second messenger in living cells, on a real-time basis. However, fluorescent proteins also have problems that the proteins are generally sensitively to pH, show high background fluorescence due to autofluorescence, and have larger molecular weights because two fluorescent proteins are linked to both termini of the target protein. Moreover, there is also a problem in terms of use, such as that a large instrumentation is required to detect fluorescence (JP-A No. 2007-49943).

A fluorescent molecular probe for detecting a second messenger, which probe utilizes bisected fragments of a single GFP molecule, has also been developed (Ozawa, T., Natori, Y., Sato, M., Umezawa, Y. Nat. Methods, 2007, 4(5): 413-419). However, the probe has the same intrinsic limitations of general fluorescent probes such as that due to the poor reversibility, when bisected GFP fragments are re-bound, the probe becomes inadequate for repeated use, and that GFP requires a long time (about 6 hours) for protein folding, and is prone to undergo misfolding.

DISCLOSURE OF THE INVENTION

Problem to be Solved by the Invention

The present invention can visualize a second messenger on a real-time basis, while taking advantages of a single-molecule-format luminescent probe which are convenient to use, stable in light emission and reproducible in ligand sensing, as a means for bioluminescence. In other words, the present invention is to provide an "in vivo and in vitro real-time bioluminescence imaging means," and the present invention provides a fusion protein which makes the object possible.

Means for Solving the Problem

Noting that the conventional methods for detecting second messengers have some sorts of problems, the present invention aims at taking full advantage of a luminescent probe which can be used conveniently, stably and repeatedly as a means for real-time visualization of a second messenger.

That is, since a luminescent enzyme has an excellent advantage that if the enzyme can be fragmentized at appropriate positions, the enzyme responds reversibly to an external signal, is not likely to be decomposed and maintains stability even in cell-free systems, and also can exhibit luminescence without any energy supply from an external light source such as a fluorescence generating apparatus if placed in an environment where the substrate is sufficiently provided, it was conceived that if the luminescent enzyme could be integrated into one molecule, the enzyme would be sufficiently applicable to the detection of second messengers which are intracellular information transmitters.

Conventional signal-molecule-format luminescent probes were designed to conceive both stimulator recognition protein (e.g., nuclear receptor) and its specific binding peptide between the fragments of a luminescent enzyme for directly detecting exogenous stimulator, whereas the present probe was devised to recognize a second reaction of the cell in response to exogenous stimulators with the incorporated conformation-changeable second messenger recognition protein. (FIG. 1 is a conceptual diagram thereof). There, attention was paid, among the second messengers, to calcium ion ($Ca^{2+}$) which controls particularly numerous in vivo physiological processes, and to calmodulin (CaM) which is representative as a recognition protein thereof.

However, since the molecular weight of calmodulin is as small as 17 KD, whereas the luminescent enzyme conventionally used as a luminescent probe is as large as about 36 to 64 KD, when the luminescent enzyme is linked to CaM inside a single molecule, steric hindrance may occur in between the respective elements of the molecular probe, and the conformational change of calmodulin due to the binding with calcium ion could not be recognized.

Thus, Gaussia princeps-derived luciferase (GLuc), which has been recently discovered and is the smallest among known luminescent enzymes, was thought to be optimal for ligand sensing, but there was no reference information upon partitioning GLuc and using it as a component of a single-molecule-format luminescent probe. Thus, the optimal partition site was unclear. Since the luminescence intensity is not significantly recovered even though the partition sites of GLuc which have been originally proposed for two-molecule-format probes are directly adopted, the active region of GLuc should be accurately reidentified so as to determine the optimum bisection site for a single-molecule-format probe, and then fine adjustment by means of linker sequence was carried out, to thus complete one aspect of the present invention.

Since GLuc imposes little burden on living cells because of its small molecular weight, and has amore intense luminescence intensity than the conventional lighting proteins (about 100 to 500 times), GLuc could contribute to an excellent single-molecule-format real-time luminescent probe which is particularly suitable for the detection of second messengers in living cells, responds reversibly to an exogenous signal (irreversible upon cancellation of the signal when the binding constant between the fragments is high) if the incorporated GLuc is partitioned at the bisection site determined by the present invention (positions 99 to 106), is able to instantaneously respond to a signal even in a cell-free system, and maintains stability without being decomposed even if temporally fragmentized. Then, the single-molecule-format luminescent probe carrying GLuc was extensively modified to determine whether the luminescent probe exhibits high molecular recognition ability and is found to be fully efficient, even in the case of using other ligand recognition proteins such as male sex hormone receptors (AR) or stress hormone receptors (GR), instead of the second messenger recognition protein. Thus, another aspect of the present invention relating to a highly versatile probe using GLuc was also completed.

Upon disposing calmodulin (CaM), which is a second messenger recognition protein, into the single molecular backbone, the inventors of the present invention first paid attention to that the degree of conformation change of CaM induced under the conditions of the presence of calcium ($Ca^{2+}$), based on the information from x-ray liquid crystal structural analysis, and found a possibility that molecular imaging based on protein conformational changes can be achieved by linking fragments of luciferase to the two termini of calmodulin (Examples 1 and 2). In this case, since the distance between the N-terminal fragment and the C-terminal fragment of GLuc flanked at both termini of CaM is shortened in the absence of $Ca^{2+}$, the luminescence value is maintained high. However, the distance between the GLuc fragments flanked at both termini of CaM is lengthened under the condition of the presence of $Ca^{2+}$, and therefore, there is provided a probe of this type in which luminescence is quenched (FIG. 1 and FIG. 5).

On the other hand, when GLuc fragments are linked to the outer side of CaM-M13, in which M13 peptide known to bind with CaM interacts with CaM under the conditions of the presence of $Ca^{2+}$, the CaM, which has undergone a conformational change upon stimulation of $Ca^{2+}$, binds to the M13 molecule inside the molecule, and as a result, the distance between the GLuc fragments is shortened, and there could be provided a luminescent probe of this type in which luminescence intensity is increased (FIG. 8). As such, the present invention provides both the luminescence value-enhancing type and the luminescence value-reducing type, and can therefore provide a means by which the user can use any type in any case according to the purpose.

Known representative examples of the second messenger include cGMP, cAMP and the like, in addition to $Ca^{2+}$, and since these second messengers vary in the size of the responding second messenger recognition protein or the degree of conformational change, it is necessary to select an optimal luciferase while taking into consideration of the steric hindrance between the respective components of the probe.

Regarding the partition site of luciferase which can be applied to a single-molecule-format in that case, it is the present invention to first determine that in the case of GLuc, the position is at nearly about half the chain length from the N-terminus; however, in the case of other luciferases, it is well known that partition can be stably achieved at a position of nearly about ⅘ of the chain length from the N-terminus, and therefore, these well known partition sites may be applied.

Furthermore, in addition to the simple mode of observing the conformational change of the second messenger recognition protein in response to a second messenger, by converting the conformational change directly to the degree of restoration of the activity of split-luminescent enzyme fragments flanked at both termini of the recognition protein, when a peptide which binds the conformation-changed second messenger recognition protein (for example, M13 peptide for calmodulin), is linked to the adjacent recognition protein, the relative position change between the partitioned luminescent enzyme fragments at both termini of the second messenger recognition protein is more amplified. In particular, in the case where the conformational change of the second messenger recognition protein is not very significant, or the like, it is preferable to employ a method of linking bisected luminescent enzyme fragments to the two termini of a fusion protein produced by linking the second messenger recognition protein and the peptide binding thereto, with a linker sequence appropriately interposed therebetween.

In conclusion, upon producing a single-molecule-format real-time luminescent probe utilizing the variance of second messenger level as an index, a second messenger recognition protein which changes its conformation in response to the binding with a second messenger is selected, and then, as necessary, a peptide sequence which selectively binds to the protein after conformational change is linked to the second messenger recognition protein, with an appropriate linker sequence interposed therebetween. Furthermore, this process also necessitates (i) selection of the optimal luciferase which can be linked to the second messenger recognition protein, (ii) determination of an appropriate bisection site in the luciferase, (iii) determination of the length of the linker to link between the respective elements constituting the probe, and (vi) examination of the degree of conformational change occurring in the case where the second messenger recognition protein binds to the second messenger, and the like.

That is, the present invention could be accomplished from the above-described findings, and specifically, the invention is as described below.

[1] A fusion protein including a single-chain protein containing a second messenger recognition protein, the N- and C-termini of which were respectively linked to an N-terminal fragment (N-LE) and a C-terminal fragment (C-LE) generated by partitioning a luminescent enzyme (LE), and the fusion protein being capable of emission or extinction of a light having a wavelength detectable by observation, as a result of a conformational change of the second messenger recognition protein induced by the binding or unbinding with a second messenger, and the subsequent association or dissociation between the N-LE and the C-LE flanked at both termini of the recognition protein.

[2] The fusion protein according to [1] above, wherein the fusion protein further includes a peptide which is capable of reversibly binding with the second messenger recognition protein, and the fusion protein can emit or extinct a light having a wavelength detectable by observation, as a result of a conformational change of the second messenger recognition protein induced by the binding or unbinding with a second messenger, followed by binding of the conformation-changed second messenger recognition protein to the peptide as brought, and the subsequent association or dissociation between the N-LE and the C-LE flanked at both termini of the recognition protein.

[3] The fusion protein according to [1] above, wherein the luminescent enzyme is Gaussia luciferase (GLuc).

[4] The fusion protein according to [1] above, wherein the second messenger is $Ca^{2+}$ ion, and the second messenger recognition protein is calmodulin.

[5] The fusion protein according to [2], wherein the peptide which is capable of reversibly binding with calmodulin which recognizes $Ca^{2+}$ ion, is M13 peptide, and the fusion protein is capable of emission or extinction of a light having a wavelength detectable by observation, as a result of a conformational change of calmodulin induced by its binding with $Ca^{2+}$ ions, followed by an interaction of the conformation-changed calmodulin with the M13 peptide, and the subsequent association or dissociation between the fragments of Gaussia luciferase flanked at both termini (N-GLuc and C-GLuc) of the recognition protein.

[6] The tandem nucleic acid molecule encoding the fusion protein according to [1] above, the nucleic acid molecule including a cDNA encoding a second messenger recognition protein, the 5'-terminus and the 3'-terminus of which were respectively linked with oligomers encoding the N-terminal fragment (N-LE) and C-terminal fragment (C-LE) generated by partitioning a luminescent enzyme (LE).

[7] The tandem nucleic acid molecule according to [6], further including, in the nucleic acid molecule, an oligomer encoding a peptide which is capable of reversibly binding with the second messenger recognition protein.

[8] An expression vector including the nucleic acid molecule according to [6] above, the expression vector being capable of expressing a fusion protein which includes a single-chain protein containing a second messenger recognition protein, both termini of which were linked with an N-terminal fragment (N-LE) and a C-terminal fragment (C-LE) generated by partitioning a luminescent enzyme (LE), or the expression vector being capable of expressing a fusion protein which further includes a peptide which is capable of reversibly binding with the adjacent second messenger recognition protein, in a transformed cell transfected with the expression vector.

[9] A transformed cell by transfection of the expression vector according to [8] above, the transformed cell expressing a fusion protein which includes a single-chain protein containing a second messenger recognition protein, both ends of which were linked with an N-terminal fragment (N-LE) and a C-terminal fragment (C-LE) generated by partitioning a luminescent enzyme (LE), or the transfected cells expressing a fusion protein which further includes a peptide which is capable of reversibly binding with the second messenger recognition protein.

[10] An analytical reagent or a kit including the analytical reagent, for detecting, identifying or quantifying a second messenger, wherein the analytical reagent includes the fusion protein according to [1] above, as an active ingredient.

[11] An analytical reagent or a kit including the analytical reagent, for detecting, identifying or quantifying a ligand which stimulates a cell surface receptor, wherein the analytical reagent includes the fusion protein according to [1] above, as an active ingredient.

[12] The analytical reagent or the kit including the analytical reagent according to [10], wherein the analytical reagent including the fusion protein as an active ingredient, or the kit including the analytical reagent, includes transformed cells themselves which have the fusion protein produced at the cell surface or within the cell.

[13] The analytical kit according to [10] above, wherein the kit including the analytical reagent has the analytical reagent immobilized on at least a part of a paper piece, a fiber segment, a microtiter plate or a probe element.

[14] An analytical reagent or a kit including the analytical reagent, for detecting, identifying or quantifying a ligand which stimulates a living cell surface receptor, wherein the analytical reagent includes the expression vector according to [8] above as an active ingredient, and the analytical reagent is transfected into a living cell and expressed within the living cell to visualize the dynamics of a second messenger.

[15] A method for detecting, identifying or quantifying a second messenger, the method including transfecting the expression vector according to [8] above into cells to express a fusion protein within the cells, and observing an increase or decrease of a light emitted as a result of a conformational change of the second messenger recognition protein induced by the binding or unbinding with a second messenger, and the subsequent association or dissociation between the N-LE and the C-LE flanked at both termini of the recognition protein.

[16] The method for detecting, identifying or quantifying a second messenger according to [15] above, wherein the occurrence that the N-LE and the C-LE are associated to or dissociated from each other, occurs as a result of a conformational change of the second messenger recognition protein induced by the binding or unbinding with a second messenger, followed by interaction of the second messenger recognition protein to a peptide which is capable of binding reversibly with the second messenger recognition protein.

[17] A method for detecting, identifying or quantifying a ligand which stimulates a cell surface receptor, the method including transfecting the expression vector according to [8] above into cells to express a fusion protein within the cells, observing the increase and decrease of a light emission as a result of a conformational change of the second messenger recognition protein induced by the binding or unbinding with a second messenger, and the subsequent association or dissociation between the N-LE and the C-LE flanked at both termini of the recognition protein, and thereby analyzing the dynamics of the second messenger in the cells.

[18] The method for detecting, identifying or quantifying a ligand which stimulates a cell surface receptor according to [17] above, wherein the occurrence that the N-LE and the C-LE are associated to or dissociated from each other, occurs as a result of a conformational change of the second messenger recognition protein induced by the binding or unbinding with a second messenger, followed by interaction of the second messenger recognition protein with a peptide which is capable of binding reversibly with the second messenger recognition protein.

[19] A method for detecting, identifying or quantifying the free calcium concentration in a physiological sample, the method including using the kit for detecting a luminescent type ligand according to [15], for a physiological or environmental sample.

[20] A fusion protein including a single-chain protein containing a ligand recognition protein, the N-terminus and the C-terminus of which were respectively linked to an N-terminal fragment (N-GLuc) and a C-terminal fragment (C-GLuc) generated by dissecting a DNA encoding Gaussia luciferase (GLuc), where an amino acid sequence in which a part or all of the amino acid residues at positions 2 to 17 have been deleted, at a partition site located at any amino acid residue at positions from 99 to 106 of the amino acid sequence inside GLuc, the fusion protein being capable of emission or extinction of a light having a wavelength detectable by observation, as a result of a conformational change of the ligand recognition protein induced by the binding or unbinding with a ligand, and the subsequent association or dissociation between the N-GLuc and the C-GLuc flanked at both termini of the recognition protein.

[21] The fusion protein according to [20] above, wherein the fusion protein further includes a peptide which is capable of reversibly binding with the ligand recognition protein, and the fusion protein can emit or extinct a light having a wavelength detectable by observation, as a result of a conformational change of the ligand recognition protein induced by the binding or unbinding with a ligand, followed by binding of the conformation-changed ligand recognition protein to the peptide, and the subsequent association or dissociation between the N-GLuc and the C-GLuc flanked at both termini of the recognition protein.

[22] The fusion protein according to [20] above, wherein the N-terminal fragment is a polypeptide including the amino acid sequence set forth in SEQ ID NO. 4, and the C-terminal fragment is a polypeptide including the amino acid sequence set forth in SEQ ID NO. 5.

[23] A nucleic acid molecule encoding the fusion protein according to [20] above.

[24] An analytical reagent or a kit including the analytical reagent, for detecting, identifying or quantifying a ligand, wherein the analytical reagent includes the fusion protein according to [20] above, as an active ingredient.

EFFECT OF THE INVENTION

The fusion protein of the present invention enables luminescence imaging on a quasi-real-time basis in both living cell systems and cell-free systems, and provides a real-time bioluminescence imaging probe having the following advantages.

(1) The probe overcomes the limits of fluorescence, and provides a very convenient bioluminescence analysis method.

(2) The probe makes possible of bioimaging of observing, on a real-time basis, biological phenomena which occur on a time scale of seconds.

(3) In contrast to the conventional probes sensing only membrane-permeable ligands, the probe in the present invention can sensitively measure even an exogenous ligand which is incapable of permeating the cell membrane (insulin, growth hormones and the like). Namely, the measurement of membrane-permeable ligands and native, endogenous ligands inside cells can be achieved with present probes. Therefore, practically all ligands can be taken as the subject of analysis, and it is now possible to achieve a wide spectrum of bioanalysis.

(4) Since it is possible to design both luminescence reduction-type and luminescence enhancement-type probes for the same ligand stimulation, the users can choose one according to their needs.

(5) The probe was devised to more efficient, simpler and more convenient by integrating ion-sensing and luminescence emission components in a single molecule. Particularly, for a cell-free system, there can be provided a luminescent probe test strip (luminescence-type ligand sensing means), which is produced by immobilizing and drying the present luminescent probe at an edge of a paper strip.

Furthermore, in the case of using GLuc fragments as the bisected luminescent enzyme at both termini of the recognition protein, since GLuc is the smallest probe among the bioluminescent probes developed thus far, the burden of the GLuc-incorporated probe on the host cell is thus extremely small, and since GLuc is very bright compared to conventional luminescent enzymes, sensitive analysis can be achieved clearly even under the conditions of intact living cells.

BRIEF DESCRIPTION OF THE DRAWINGS

FIG. 1 shows (A) the conformational change of a recognition protein (calmodulin; CaM) for $Ca^{2+}$, which is a representative second messenger recognition protein in cells, induced by ligand stimulation, and (B) a conceptual diagram of a luminescent probe based on the conformational change. It can be seen from the diagram that the N-terminus and the C-terminus of CaM are approaching closer in the absence of $Ca^{2+}$, while when $Ca^{2+}$ binds to CaM, the N-terminus and the C-terminus of CaM are separating away;

FIG. 2 shows (A) a construction diagram for a single-molecule-format real-time probe incorporated with calmodulin (CaM), (B) measurements of ligand sensitivity of various probes, and (C) a diagram showing changes in the X-ray liquid crystal structure of calmodulin within the respective probes. The probe is constructed such that the overall length of GLuc or FLuc is bisected, and between the bisected fragments, M13-fused CaM which is a $Ca^{2+}$ recognition protein, has been interposed, or only CaM has been interposed;

FIG. 3 shows the determination of an appropriate dissection site of Gaussia Luciferase (GLuc). (A) shows the specific dissection sites within the GLuc, and (B) shows the intensities of bioluminescence of the luminescent probes obtained on the basis of various dissection sites. Dissection sites #4 and #5 are most probable. (C) represents a diagram showing the hydrophobicity distribution in the amino acid sequence constituting the GLuc. It can be seen that a hydrophilic region is present between amino acid residue 90 and amino acid residue 100;

FIG. 4 shows the spectra of the luminescence intensities by CaM probes produced through point mutation of each of the amino acid residues present between dissection sites #3 and 4 of Gaussia Luciferase (GLuc), to glycine. (A) shows the mutated positions, and (B) shows the spectra of the luminescence intensities changed by the respective mutations;

FIG. 5 shows (A) measurements of the ATP-concentration dependency of a luminescent probe with split-GLuc fragments dissected at site #5, and (B) a conceptual diagram showing the conformational change of this luminescent probe. For example, an ATP receptor which is an endogenous membrane receptor of COS-7 cells, is stimulated by 100 mM ATP, to thereby increase the concentration of $Ca^{2+}$. CaM in the probe responds to the elevated $Ca^{2+}$ Level, and as a result, the luminescence intensity is reduced. This phenomenon depends on the ATP concentration;

FIG. 6 shows (A) an example of real-time bioluminescence imaging using the optimal CaM probe, and (B) a prototypical luminescence spectrum by pSica-5. It can be seen that bioluminescence from living cells fluctuate in response to external stimuli. Also, as can be seen from (B), the luminescence intensity is decreased in a stimulus-dependent manner;

FIG. 7 shows (A) time-course of the $Ca^{2+}$ concentration-dependent luminescence intensity of living cells transfected with pSica-5, which is an optimal CaM probe, and calibration curves (B). These are all the results of measuring the fluctuation in bioluminescence after introduction of a stimulus to intact living cells;

FIG. 9 shows measurements of the ligand sensitivity of AR LBD or GR LBD, which has both fragments of GLuc dissected at the optimum dissection site (dissection site #5; G106/G107) at the two termini. (A) represents the DNA construct, (B) shows the steroid hormone sensitivity of a probe containing AR LBD (pSimar), and (C) shows the sensitivity to steroid hormones of a probe containing GR LBD (pSimgr); and FIG. 10 shows the $Ca^{2+}$ sensitivity of a luminescent probe mounted and dried on a nitrocellulose paper piece constructed on a glass plate. (A) represents an actual photograph of a cross-shaped sensor strip constructed on a glass plate, with each end circle having a diameter of 1 cm. (B) shows the respective positions of the probes mounted on the terminal circle of the sensor strip, and (C) shows the $Ca^{2+}$ sensitivity of the present sensor strip. It can be seen that strong luminescence emits under the conditions of the presence of $Ca^{2+}$ ion (white spot). On the other hand, it can be also seen that under the conditions of the absence of $Ca^{2+}$ ion, the luminescence is as weak as to be indiscernible. (D) shows the profile of the $Ca^{2+}$ ion-dependent increase in luminescence value of the luminescent strip formed on the glass plate.

BEST MODE FOR CARRYING OUT THE INVENTION

Figure 8:
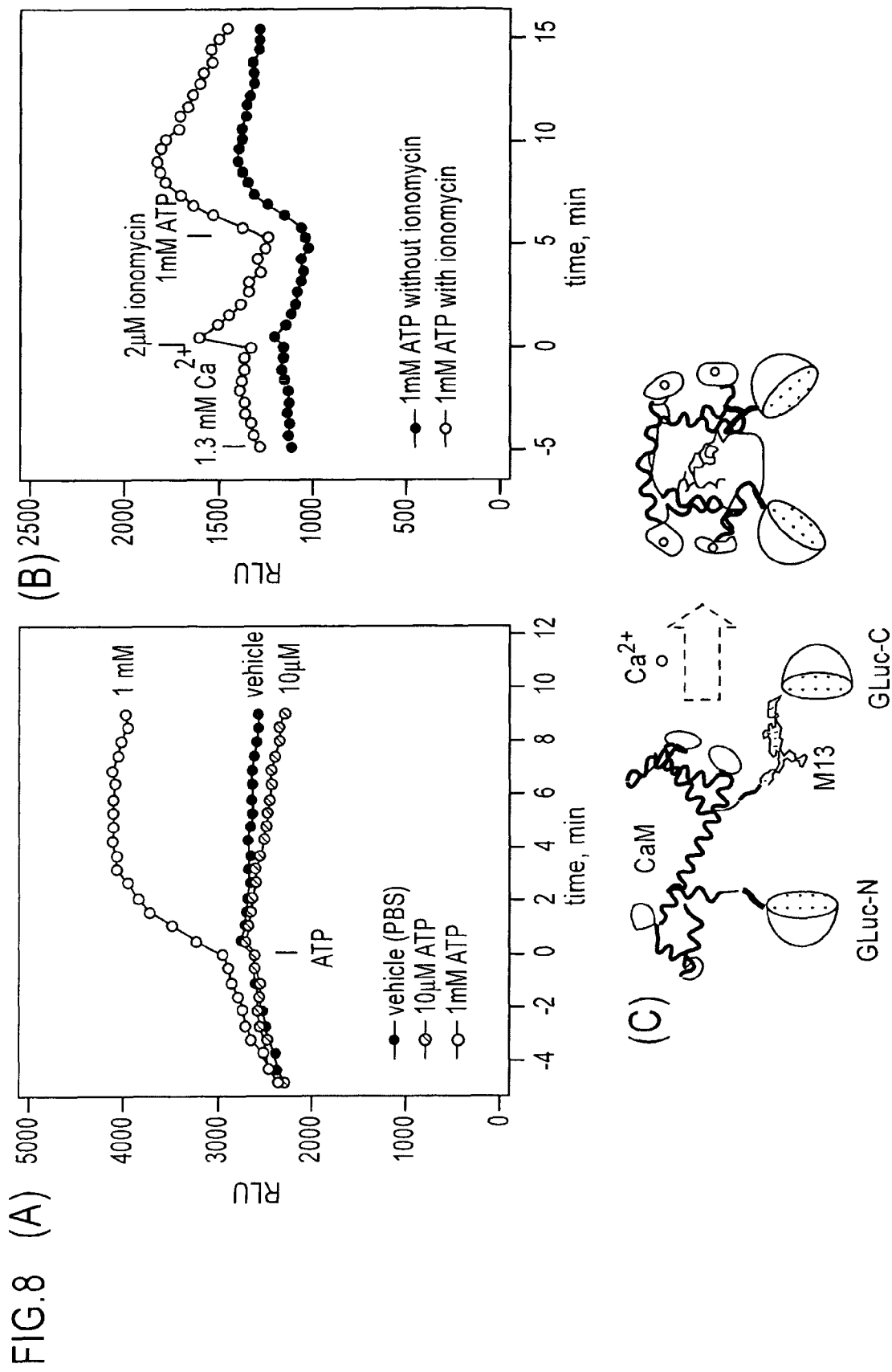
FIG. 8 shows (A) time-course of the bioluminescence intensities from the cells transfected with pSicam, which is an optimized CaM-M13 probe, in response to a stimulator, (B) variances in the luminescence intensities which depend on the ionomycin or ATP levels, and (C) a conceptual diagram for the mechanism of molecular response of the CaM-M13 probe. It can be seen that before and after the binding of CaM and M13, the distance between the two protein termini approaches from 95.14 Å to 50.52 Å.

The fusion protein of the present invention is used as a single-molecule-format real-time luminescence imaging probe, and is a fusion protein including, as the constituent elements, (i) a second messenger recognition protein, (ii) optionally, a peptide which is capable of reversibly binding with the second messenger recognition protein, and (iii) a partitioned luminescent protein (LE), fragments of which are disposed at the two termini of the fusion protein backbone, and (iv) the fusion protein is a single-chain fusion protein in which the respective constituent elements are linked with or without appropriate linkers interposed therebetween. The fusion protein of the present invention can emit or extinct light having a wavelength detectable by observation, as a result of a conformational change of the second messenger recognition protein induced by the binding or dissociation with a second messenger, and subsequent association or dissociation of the N-LE and C-LE at both termini of the recognition protein. Furthermore, in the case of including the (ii) peptide which is capable of reversibly binding with the second messenger protein, the fusion protein can emit or extinct a light having a wavelength detectable by observation, as a result of a conformational change of the second messenger recognition protein induced by the association or dissociation with a second messenger, followed by binding of the second messenger recognition protein to the peptide as brought by the conformational change, and the subsequent association or dissociation of the N-LE and the C-LE at both termini of the recognition protein. That is, when a living cell membrane receptor is activated by external stimuli, the fusion protein of the present invention can achieve real-time imaging of the increase or decrease of the second messenger level induced under the immediate influence of the receptor activation in living cells, and thus the fusion protein can be used in an analysis kit even under a non-cellular environment. Hereinafter, the fusion protein of the present invention may also be referred to as a "single-molecule-format real-time luminescent probe," or simply a "probe," from the functional aspects.

The "single-molecule-form at real-time luminescent probe" of the present invention is a probe capable of real-time imaging, of various rapid secondary molecular phenomena triggered by the membrane surface receptor of living cells upon activation of the receptors induced by the specific ligands, and is characterized in that all of the elements are optimally integrated in a single fusion molecule. Specifically, the probe is a fusion protein having the above-mentioned elements (i) to (iii) as the fundamental elements. Each of the component proteins or peptides can be obtained by a gene recombination method, a chemical synthesis method or the like, and then all the elements can be chemically linked; however, the fusion protein probe is typically produced when an expression vector subcloned with an inserted chimera DNA in which the DNAs encoding the respective components are tandemly linked, is expressed in living cells. Here, the term "chimera DNA" means a DNA in which several DNA fragments of different origins are artificially linked in a linear chain form, and which is capable of expressing a fusion protein molecule having proteins or peptides as components. The chimera DNA according to the present invention is a DNA molecule capable of expressing a fusion protein which functions as a single-molecule-format real-time luminescent probe within living cells or even in cell-free conditions.

Genes encoding these various components are subcloned into an expression vector as a chimera DNA in which the DNAs encoding the respective components are tandemly linked, so that the components constitute a linear fusion protein molecule after expression.

An expression vector which includes a DNA encoding the single-molecule-format real-time luminescent probe of the present invention, carries a control sequence capable of gene expression in cells, is transfected into living cells. When the intracellular phenomena involving a second messenger which is induced as secondary to a test, is subjected to the imaging using the single-molecule-format real-time luminescent probe expressed in living cells, the nature, concentration and activity of the test substance can be analyzed. In other words, the second messenger itself can be detected, identified or quantified with the probe. At the same time, the initial external ligand which stimulates the cell membrane surface receptor can also be indirectly detected, identified or quantified.

The term "living cells" according to the present invention refers to the original living cells of an organism (prokaryotic cells, yeast cells, insect cells, and cells of mammalian animals including human being), as well as cultured cells in a state of the original functions being maintained (prokaryotic cells and eukaryotic cells), or cells transplanted and infected into an organism. Typically, the living organisms mean an experimental animal such as mouse, or cells thereof.

As for the "expression vector" as used in the present invention, known expression vectors for eukaryotic or prokaryotic cells can be used without particular limitation. Furthermore, in order to control the expression of the probe derived from the above-described chimera DNA (for example, expression in certain tissue in an individual organism, or expression by a certain ligand/stimulant), a known tissue-specific or certain stimulus-specific promoter sequence may also be incorporated therein. A probe-expressing vector can be transfected into cells by, for example, a microinjection method, an electroporation method, or a transfection method using a lipid reagent (TransIT, Mirus). Furthermore, by not only simply imposing a role of expression of the probe on the expression vector transfected by these techniques, but also ligating a control sequence which is capable of controlling expression, in the upstream of the probe, an additional bioanalysis system can be designed, for instance, to utilize the presence or absence of expression of the probe itself as an index.

Furthermore, when a chimera DNA encoding the present probe is linked to a retrovirus vector such as pMX, and is transfected into a packaging cell plate having a capability to produce high-titer virus, a retrovirus capable of infecting animals can be produced. If various organs of animals are infected with this virus, real-time imaging characteristic to second messengers within various organs can be achieved.

The term "ligand" according to the present invention means a substance which is capable of binding specifically to a certain protein on the cell membrane or within a living cell and changing the function of the protein. For example, the ligand refers to steroids or synthetic chemical substances for nuclear receptors, various cytokines for cytokine receptors, and stimulating substances including insulin for cell membrane receptors such as insulin receptors.

Hereinafter, the respective components of the single-molecule-format real-time luminescent probe will be described.

The "second messenger recognition protein" according to the present invention refers to a protein which binds with a "second messenger" occurring in cells by extracellular stimuli, and undergoes a change in the conformation. Thereby, it becomes possible to observe conformational changes of the second messenger recognition protein which are dependent on the concentration changes of the "second messenger." In that case, it is preferable that the second messenger recognition protein be characterized by undergoing a conformational change, and being capable of reversibly binding to or dissociating from a part of another protein or a peptide fragment thereof (hereinafter, simply referred to as "peptide").

The term "second messenger" as used herein means an intracellular signal transmitter of a different category, which is newly generated inside cells as a result of stimulation of an extracellular signal transmitter such as a hormone or a neurotransmitter binding to a receptor present in the cell membrane. For example, cGMP, cAMP, PIP, PIP2, PIP3, inositol trisphosphate (IP3), IP4, $Ca^{2+}$, diacylglycerol, or arachidonic acid can be used as the object.

Preferred combinations of these second messengers and second messenger recognition proteins recognizing them will be shown below.

As the $Ca^{2+}$ recognition proteins which recognizes second messenger $Ca^{2+}$, there may be mentioned calmodulin (CaM), recover in and the like, and as the cAMP recognition protein which recognizes cAMP, there may be mentioned cAMP-gated cation channel and protein kinase A (PKA). As the diacylglycerol recognition protein which recognizes diacylglycerol, protein kinase C (PKC) can be used. Furthermore, cGMP-gated $Na^+$ channel may be mentioned as the cGMP recognition protein which recognizes cGMP.

The term "peptide which is capable of reversibly binding with the second messenger recognition protein" according to the present invention refers to a "peptide" which can reversibly bind to or dissociate from the second messenger recognition protein, in response to a conformational change based on the activation of the second messenger recognition protein as a result of binding with a second messenger. Essentially, the peptide may be a long protein domain, or may also be a short peptide.

For example, with regard to calmodulin (CaM), M13 which is a peptide derived from myosin light chain kinase (26 amino acid residues: KRRWKKNFIAVSAANRFKKISSS-GAL) is preferably used. Furthermore, in additional M13, there may be mentioned CaM-dependent protein kinases such as adenylyl cyclase and calmodulin kinase II, as the protein capable of binding to calmodulin. Portions of these proteins may also be used instead of the M13 to visualize the binding with CaM.

The "luminescent enzyme (LE)" according to the present invention can be partitioned into an N-terminal fragment and a C-terminal fragment (respectively named N-LE and C-LE), and is preferably firefly luciferase (FLuc), Renilla luciferase (RLuc), Gaussia luciferase (GLuc), Click Beetle luciferase (CBLuc), or the like. In the Examples of the present invention, Gaussia luciferase (GLuc) was used.

These LE's are known in terms of the amino acid sequence or the DNA base sequence (for example, GenBank/AB062786 or the like for FLuc, GenBank/AY258592.1 or the like for CBLuc, GenBank/AY015993 or the like for GLuc), and it is possible to obtain the DNA based on such sequence information, by a known method.

The "partitioned luminescent enzyme (LE)" means that the luminescent activity is temporarily inactivated by bisecting a single-molecular LE. It is necessary that LE be dissected at a site where the two partitioned LE fragments are suitably re-constructed such that the enzyme activity can be recovered by the interaction between the segments. Here, the partition site is represented by the position of amino acid residue. For example, when GLuc (amino acid residue 1 to residue 185) is said to be partitioned at a position of 99, partition is achieved between the position 99 and the position 100, and the phrase has the same meaning as the expression that the protein is dissected at a position of 99/100.

Such position for bisecting the LE can be appropriately determined by referring known databases or the like, and usually, an LE loses its light by partitioning if the existing hydrophilic region positioned at ⅘ of the chain length from the anterior end is appropriately dissected. Thus, the partition site at which light is emitted by reassembly of the fragments, can be determined simply. For example, in the case of FLuc, as disclosed in Non-Patent Document 6, the protein can be dissected at a position of 437/438 of the amino acid sequence, and in the case of CBLuc, the protein can be dissected at a position of 412/413 as shown in the Examples that will be described later. In the case of RLuc, as disclosed in WO 2004/104222 (in the case of two-molecule-format), the protein can be partitioned at an appropriate site, but if dissected at a position of 91/92 of the amino acid sequence, the luminescence intensity obtained after reassembly of the fragments becomes the highest. Furthermore, in the case of CBLuc, the protein can be bisected at a position of 439/440, 412/413 or the like of the amino acid sequence. Also, as shown in the Examples that will be described later, an N-terminal fragment (N-LE) and a C-terminal fragment (C-LE) having some parts overlapping or deleted, may also be used.

However, GLuc is distinguished from other luciferases in the aspects that the protein has a hydrophilic region at a position close to the center of the whole amino acid sequence, the liquid crystal structure has not yet been elucidated, and the protein has an extracellular secretion signal sequence at the N-terminus.

In regard to the two-molecule-format luminescent probe, various examples of investigation have been reported on the partition sites for making the N-terminal fragment and the C-terminal fragment associated inside GLuc, and the results show that partition at the amino acid position of 109 is considered to be optimal. In fact, when two fragments obtained by partitioning the protein at this position, are linked separately to biotin and avidin, respectively, luminescence property is efficiently restored (Remy, I., and Michnick, S. W. Nat. Methods, 2006, 3, 977-979).

However, this partition site cannot be directly applied to the single-molecule-format luminescent probe of the present invention. That is, when the N-terminal fragment and C-terminal fragment of GLuc obtained by partitioning at the position suggested in Remy, I., and Michnick, S. W. Nat. Methods, 2006, 3, 977-979, are linked to two termini of a single chain polypeptide containing a second messenger recognition protein, the subsequent luminosity cannot be sufficiently restored after reassembly.

The inventors of the present invention examined in detail the optimal partition sites of GLuc to be used for the single-molecule-format luminescent probe of the present invention (Example 2), and determined that the partition site is present at any amino acid residue at positions from 99 to 106 of the amino acid sequence. Since the hydrophobic signal sequence portion on the N-terminal side (positions 2 to 17) in the N-terminal fragment can be deleted, and thereby the overall size of the luminescent probe is decreased, the burden imposed on the cells is highly relieved by introduction and expression of the fragments into living cells, which is preferable. Additionally, the methionine (M) residue at the N-terminus is essential for the expression of the fragment in cells by the genetic recombination method. That is, the fusion protein is characterized as a single-chain protein containing a second messenger recognition protein, and linked respectively to the N-terminus and the C-terminus thereof, where an N-terminal fragment (N-GLuc) and a C-terminal fragment (C-GLuc) generated by partitioning GLuc in which a part or all of the amino acid residues at positions 2 to 17 have been deleted, at a partition site located at any amino acid residue from 99 to 106 of the amino acid sequence constituting the GLuc. GLuc can be partitioned into an N-terminal fragment formed from the amino acid sequence of SEQ ID NO. 4, which was deleted a portion from position 2 to position 17 of SEQ ID NO. 4, and a C-terminal fragment formed from the amino acid sequence of SEQ ID NO. 5. The two fragments do not emit light if they are positioned distant from each other, while emitting light when positioned sufficiently close to each other. This polypeptide set formed from the two fragments can be said to be a novel and useful polypeptide set, and is a particularly suitable set for the real-time luminescent probe of the present invention, which is combined with a second messenger recognition protein for detecting the intracellular phenomena resulting from generation of a second messenger. Furthermore, this polypeptide set, when linked to the two termini of a polypeptide containing not a second messenger recognition protein but some other general ligand recognition protein, undergoes emission or extinction of light in response to a conformation change of the ligand recognition protein resulting from the binding to a ligand, and can therefore be used as a luminescent probe which is capable of directly detecting the ligand.

The respective components constituting the probe of the present invention may be in some cases directly linked in a tandem order, but the elements are usually linked via "linker sequences." In that case, the length of the linker serves as an important factor for determining the performance of the luminescent probe (Kim, S. B., Kanno, A., Ozawa, T., Tao, H., Umezawa, Y. ACS Chem. Biol. 2007, 2(7), 484-492). By varying the kind and length of the linker sequence upon linkage, the distances between the respective components can be appropriately adjusted, and as a result, fine adjustment of the positions of the bisected luminescent enzyme fragments at the two termini can be achieved. The linker as used herein is preferably a peptide sequence, so that the probe of the present invention may be expressed as a single-chain fusion protein. In particular, it is preferable that the second messenger recognition protein and the second messenger recognition protein-interacting peptide contain amino acids having highly flexible amino acids with less steric hindrance (glycine (G), alanine (A), etc.) as the main components so that the second messenger recognition protein and the ligand approach and bind with each other upon the binding of the ligand to the protein, and are also linked via a linker peptide to which some serine (S) residues have been added (typically, a GS linker having a sequence in which glycine and serine are repeated), in order to impart hydrophilicity. In the instant Examples, a linker sequence equivalent to 5 amino acid residues, which is formed from glycine (G) residues, was used, but usually, the respective components are linked via a linker peptide which mainly contains glycine (G) and/or serine (S) and has a length of about 1 to 10 amino acid residues. An optimal linker that can be used is a GS linker having 5 to 10 amino acid residues. As such, when a "soft linker" having flexibility is used, the fusion protein can acquire flexibility at the time when the bisected luminescent enzyme fragments at both termini restore luminosity.

Furthermore, upon tandem linkage of the DNAs encoding the protein or peptide of the respective constituent elements, restriction enzyme cleavage sites will be provided at both termini of the respective DNAs, but in that case, codons encoding restriction enzyme cleavage sites may be added thereto, and as a result, the supplemented amino acid residues consequently constitute an additional linker sequence.

Therefore, in the present invention, the "single-chain protein containing a second messenger recognition protein" or the like will be described while omitting the presence of the linker sequence, but the invention appropriately encompasses the cases where linker sequences each equivalent to 1 to 10 amino acid residues are interposed between the respective elements.

Table 1 below shows (i) target membrane receptors which may be the object of the present technique, (ii) physiological phenomena induced thereby, and (iii) the type of the second messengers, which serve as intracellular signal transmitters connecting the previous two items.

For the luminescence imaging of specific second messengers in cells elevated by other external stimuli, a probe can be respectively constructed by linking LE fragments obtained on the basis of the appropriate partition site of an LE, a second messenger recognition protein, and if necessary, a peptide which is capable of binding with the second messenger recognition protein, based on the above-described linking order. DNA insertion into an expression vector can be easily carried out by those having ordinary skill in the art, and appropriate linking order can also be suitably confirmed by few trials.

The term "qualitative and quantitative analysis of an intracellular second messenger activity induced by an external stimulus" according to the present invention means that either one of the subject luminescent probes which have been expressed in advance in living cells, recognizes a second messenger generated in the cells as a secondary signal

TABLE 1

List of secondary signal transmitters (second messengers) induced by external stimuli, and consequent cellular responses

| Internal organ | External stimulus | Cell membrane receptor | Secondary signal transmitter(second messenger) induced by cell membrane receptor activity | Consequent cellular response induced by second messenger |
| --- | --- | --- | --- | --- |
| Thyroid gland | Thyroid-stimulating hormone (TSH) | TSH receptor | CAMP | Secretion of thyroid hormones |
| Adrenal cortex | Adrenocorticotropic hormone (ACTH or corticotropin) | ACTH receptor | CAMP | Secretion of stress hormones |
| Ovary | Luteinizing hormone (LH) | luteinizing hormone/ choriogonadotropin (LHCG) receptor | CAMP | Secretion of luteal hormones |
| Muscle | Adrenalin | β-adrenergic receptor | CAMP | Decomposition of glycogen |
| Bone | Parathyroid hormone (PTH; parathormone) | PTH receptor | CAMP | Bone absorption |
| Heart | Adrenalin | β-adrenergic receptor | CAMP | Increase of heartbeat and contraction |
| Liver | Glucagon | glucagon receptor | CAMP | Decomposition of glycogen |
| Kidney | vasopressin | vasopressin receptor | CAMP | Water absorption |
| Fat | Adrenalin, ACTH, glucagons, TSH | β-adrenergic receptor, ACTH receptor, glucagon receptor, TSH receptor | CAMP | Decomposition of triglyceride |
| Liver | vasopressin | vasopressin receptor | $Ca^{2+}$ | Decomposition of glycogen |
| Pancreas | acetylcholine | acetylcholine receptor | $Ca^{2+}$ | Secretion of amylase |
| Smooth muscle | acetylcholine | acetylcholine receptor | $Ca^{2+}$ | Muscle contraction |
| Mast cells | antigen | antigen receptor | $Ca^{2+}$ | Secretion of histamine |
| Blood platelets | thrombin | thrombin receptor | $Ca^{2+}$ | Blood clotting |

The above-described respective components can be linked in any order, with the proviso that dissected LE fragments are disposed at the two termini. However, in between the two fragments, only one second messenger recognition protein may be present (n=1), or a peptide which is capable of binding with the second messenger recognition protein may also be added (n=2).

In regard to specific probe constitution, a luminescence-value-decreasing-type probe has a constitution of [N-LE/CaM/C-LE] from the N-terminal side, and a luminescence-value-increasing-type probe has a constitution of [N-LE/CaM/M13/C-LE]. However, for the luminescence-value-increasing-type probe, essentially no problem arises even with a constitution of [N-LE/M13/CaM/C-LE] from the N-terminal side.

induced by an external stimulating substance, which is the test substance, and using the subsequent wavelength and intensity of the light emitted as an index, the nature and the degree of activity of the external stimulus which is the test substance, are determined. The real-time measurement of the luminescence intensity makes use of a commercially available luminescence plate reader.

In regard to the method for detection, identification or quantification of the present invention, typically, living cells which have been transfected using an expression vector carrying a DNA sequence encoding the single-molecule-format real-time luminescent probe, are stimulated by the test substance, and the intensity of thus emitted light is measured (in vivo imaging) Furthermore, qualitative and quantitative analysis of a stimulator can be made possible by providing the subject probe expressed from the above-described living cells, on an end side of a paper strip, and dripping the stimulating substance on the other strip end (in vitro imaging).

As for the cell-free luminescence imaging means of the present invention, there can be provided a luminescence-type ligand sensing means in which the luminescent probe of the present invention is mounted and dried at the ends of a paper piece, a fragment plate, a probing device or the like. As for the material, a paper piece formed of nitrocellulose paper or the like, or a polymer strip formed of nylon 66, polyvinylidene fluoride, a hydrophobic polymer or the like is used. In particular, when a nitrocellulose paper piece is used, a luminescent probe-attached type test paper which is easy to handle like in the case of litmus paper, can be provided.

As such, since the probe of the present invention has all elements necessary for the stimulant sensing and luminescence signal emission integrated in a single molecule, if the present probe is attached to the ends of a paper piece, various bioactive small molecules present in physiological samples, such as calcium, can be targeted. Therefore, for various physiological samples (blood, urine, sweat and saliva), if the corresponding kits are respectively used, the concentrations of various bioactive substances can be measured as an index for a person's state of health. Therefore, a user can conveniently measure the state of health of oneself. For example, the calcium concentration in a blood sample is an important index directly related to the state of bone mineralization, the blood coagulation system, and the maintenance of cell membrane potential.

The luminescent probe provided in the kit can utilize the fusion protein of the present invention in a purified state or even in an unpurified state, after the production thereof by synthesis or by a genetic recombination technique, but transfected cells which are expressing a recombinant fusion protein can also be directly used. In that case, the transfected cells can emit or extinct light in response to the generated levels of a second messenger in the cells on a real-time basis, and can therefore be utilized as a cellular sensor which identifies and quantifies various bioactive small substances stimulating the receptors on the cell surface. The cellular sensor may also serve as a research tool for basic bioscience fields, which is useful for elucidation of intracellular molecular mechanisms involving hormones, drugs and chemical substances. Furthermore, in various areas and organs in vivo, the activity of bioactive small substances such as calcium can be subjected to visualization imaging, without imposing large burden on the cells. The tool is different from the conventional imaging tools for in vivo molecular phenomena, which tools are based on physical molecular phenomena as in the case of MRI, and the tool of the present invention is characterized in that the presence or absence of any specific in vivo molecular phenomenon can be determined in a pinpoint manner. For example, in an animal experiment, a transgenic mouse can be produced using a gene encoding the present fusion protein, and contraction of muscles caused by fluctuation of $Ca^{2+}$ can be specifically visualized. Thereby, specific molecular imaging of a place where motion (muscular contraction) occurs in vivo can be made possible, and thus such imaging is greatly helpful to the identification of risk factors for diseases associated with muscular atrophy, elucidation of the molecular mechanism, and the like.

By taking out the probe from the above-described cells, and using the probe, in a purified state or even unpurified state, while mounted on a paper piece, the calcium concentration in a physiological sample can be measured as an example of various bioactive small molecules, and thereby rapid diagnosis of diseases such as hypercalcemia and osteoporosis is made possible.

The single-molecule-format real-time luminescent probe of the present invention can be expressed in large quantities not only in the above-mentioned eukaryotic cells, but also in prokaryotic cells such as bacteria cells. In the case of eukaryotic cells, a large amount of the probe in the culture medium supernatant which can be used in analyses even without going through purification processes, may be harvested by ligating an appropriate secretion signal sequence (MGVKVLFALI-CIAVAEA or the like), and allowing the cells to secrete the probe in large amounts into the medium. Furthermore, in the case of prokaryotic cells, a purified single-molecule-format real-time luminescent probe can be obtained in large quantities, by attaching a tag for column purification (for example, His Tag; HHHHHH). A kit combining a paper strip having these purified single-molecule-format real-time luminescent probes, with the substrate of the luminescent enzyme, can constitute a kit capable of qualitative and quantitative analysis of an external stimulus and a second messenger which is a secondary phenomenon resulting from the external stimulus, in the same manner as in those kits utilizing living cells which express these luminescent probes.

In order to carry out ligand analysis or screening using the single-molecule-format real-time luminescent probe, the following method using living cells can be applied, but the invention is not limited to this method.

(i) A plasmid having a DNA which encodes a single-molecule-format real-time luminescent probe, is transfected into living cells on a 24-well plate, and the cells are cultured for 16 hours.

(ii) The culture medium for the cells is removed, and in place thereof, 200 mL of a buffer solution (for example, HBSS buffer) containing a substrate (coelenterazine) is added to immerse the cells.

(iii) The cells are stimulated with a specific stimulating substance, and the values of luminescence change before and after the stimulation are monitored using a luminescence plate reader (for example, LB 941 Multimode Reader (Berthold)).

As an experiment for a cell-free system (in vitro) using the single-molecule-format real-time luminescent probe, the following analysis and screening can be carried out, but the invention is not limited to this method.

(i) A purified single-molecule-format real-time luminescent probe is directly mounted on the ends of a 1.2 cm-long cross-shaped paper strip, and dried.

(ii) 15 µL of a substrate solution containing a stimulating substance is added dropwise at the center of the cross-shaped paper strip, and immediately the luminescence value is measured using a luminescence scanner (for example, RAS-3000; FujiFilm).

As such, as the kit for screening of the present invention, in addition to the kit including living cells which have been transfected using an expression vector containing a nucleic acid encoding the single-molecule-format real-time luminescent probe, use can also be made of a kit combining an expression vector containing a nucleic acid encoding the single-molecule-format real-time luminescent probe with the substrate for the luminescent enzyme carried by the probe, and a kit combining a luminescent strip mounted with the single-molecule-format real-time luminescent probe at the ends, with the specific substrate for the luminescent enzyme.

Other terms or concepts according to the present invention are stipulated in detail in the detailed description of the invention or Examples. In addition, the terms are basically based on the IUPAC-IUB Commission on Biochemical Nomenclature, or based on the meanings of the terms that are conventionally used in the pertinent field. Furthermore, various technologies used to carry out the present invention, particularly excluding the technologies with their sources specified, can be easily and certainly carried out by a person having ordinary skill in the art based on known literatures. For example, the technologies related to genetic engineering and molecular biology can be carried out by the methods described in J. Sambrook, E. F. Fritsch & T. Maniatis, "Molecular Cloning: A Laboratory Manual (2nd edition)," Cold Spring Harbor Laboratory Press, Cold Spring Harbor, New York (1989); D. M. Glover et al. ed., "DNA Cloning," 2nd ed., Vol. 1 to 4, (The Practical Approach Series), IRL Press, Oxford University Press (1995); Ausubel, F. M. et al., Current Protocols in Molecular Biology, John Wiley & Sons, New York, N.Y., 1995; The Japanese Biochemical Society, ed., "Lectures on Biochemical Experiments, Second Series, 1, Methods in Gene Study II," Tokyo Kagaku Dojin (1986); The Japanese Biochemical Society, ed., "Lectures on Biochemical Experiments, Second Series, 2, Nucleic acids III (Recombinant DNA Technology)," Tokyo Kagaku Dojin (1992); R. Wu ed., "Methods in Enzymology," Vol. 68 (Recombinant DNA), Academic Press, New York (1980); R. Wu et al., ed., "Methods in Enzymology," Vol. 100 (Recombinant DNA, Part B) & 101 (Recombinant DNA, Part C), Academic Press, New York (1983); R. Wu et al., ed., "Methods in Enzymology," Vol. 153 (Recombinant DNA, Part D), 154 (Recombinant DNA, Part E) & 155 (Recombinant DNA, Part F), Academic Press, New York (1987) and the like, or the methods described in documents cited in the above-mentioned literatures, or methods that are substantially equivalent to those methods or methods modified therefrom. Furthermore, various proteins and peptides used in the present invention, and DNAs encoding the proteins and peptides are available from existing databases.

EXAMPLES

Hereinafter, the present invention will be described specifically and in more detail by way of Examples, but the present invention is not intended to be limited to the following examples. Furthermore, the luminescent enzyme applicable to the real-time imaging probe is not intended to be limited to GLuc, but explanations will be given focusing on GLuc.

Example 1

Construction of Plasmid Carrying Nucleic Acid Molecules which Encode Various Fusion Proteins for Single-molecule-format Luminescent Probe Containing Calmodulin (CaM) for $Ca^{2+}$ Recognition The subject probe which is capable of imaging, on a real-time basis, the response phenomena induced by external stimuli in living cells, will be designated as Simor probe, based on its name in English (a SIngle-MOlecule-format bioluminescent probe for Realtime imaging). A probe comprising calmodulin (CaM) will be designated as Sica. On the other hand, a probe comprising calmodulin as well as calmodulin recognition peptide sequence (M13), will be designated as Sicam. The eukaryotic expression vectors incorporated with the respective probes will be respectively designated as pSica and pSicam.

PCR amplification was carried out to introduce KpnI and BamHI, which are restriction enzyme sites, into the two termini of a cDNA encoding calmodulin, which is a *Xenopus laevis* (African clawed frog)-derived $Ca^{2+}$ recognition protein (CaM; 1-150 AA; GenBank/NM001087395). On the other hand, as an optimal luminescent enzyme which can be linked to the CaM as a single-molecule-format probe, Gaussia princeps-derived luciferase (GLuc; 1-189 AA; GenBank/AY015993) was used. Five fragment pairs were generated by fragmentizing five sites of the cDNA of GLuc by PCR reaction, and were used in the examination of the optimal partition sites for GLuc (FIG. 3), which will be discussed in Example 2.

As shown in FIG. 2, a cDNA construct capable of expressing a fusion protein in which CaM is linked in the form of being interposed between the N-terminus and the C-terminus of GLuc (GLuc-N and GLuc-C), was produced. Furthermore, there was generated an additional cDNA construct capable of expressing a fusion protein in which, M13-linked CaM was sandwiched between the N-terminus and the C-terminus of GLuc, finally subcloned into pSica-5.

As a device to just allow that the expression of the probe to be conducted in living cells, be achieved through the intrinsic physiological processes of the living cells, which represent the object of analysis, and not to impose burden on the living cells, the inventors of the present invention conceived of the graph of the hydrophobicity distribution of GLuc and the respective roles of the domains in GLuc, and presupposed that the amino acid residues 2 to 17 from the anterior end of GLuc would not have any influence on the luminescence activity. Thus, the inventors designed the probe of the present invention in a form not containing the amino acid residues of this range. As a result, a luminescent probe could be produced in a form having the total molecular weight of GLuc reduced by approximately 11%.

Furthermore, according to the present invention, the respective elements within the probe are designed such that typically about 4 to 5 residues of glycine (G) and/or serine (S) are interposed between the respective elements, but in the present Example, a glycine (G) linker sequence having a length equivalent to 5 amino acid residues is used. If the probe is depicted while omitting this linker sequence, the probe of the present Example can be represented by [GLuc-N/CaM/GLuc-C] or [GLuc-N/CaM/M13/GLuc-C], and the gene construct was subcloned into the skeleton of pcDNA3.1 (+) vector (Invitrogen) to construct a plasmid. In addition, the sequence of the constructed plasmid was confirmed using BigDye Terminator Cycle Sequencing kit and ABI Prism310 gene analyzer. The plasmids comprising only CaM between the N-terminal fragment and C-terminal fragment of GLuc were referred to as pSica series (pSica-1 to pSica-5).

As a control group, a gene construct of [FLuc-N/CaM/FLuc-C] or [FLuc-N/CaM/M13/FLuc-C] was produced for the case of using FLuc-N and FLuc-C, which are fragments of firefly luciferase (FLuc), and the gene construct was subcloned into the backbone of pcDNA3.1(+) vector (Invitrogen) in the same manner.

Example 2

Examination of Partition Site of GLuc

The inventors of the present invention presupposed, on the basis of the analysis of hydrophilicity distribution search in the total amino acid sequence of GLuc, that a hydrophilic region of amino acid residues at positions 90 to 108 in the amino acid sequence of GLuc was the region between the two protein domains constituting GLuc. Thus, the inventors determined five partition sites inside the above-mentioned region, and produced five fragment pairs by fragmentizing five sites of the cDNA of GLuc by PCR reaction, as previously described (FIG. 3).

The plasmids carrying only CaM between these five pairs of N-terminal fragment and C-terminal fragment of GLuc, were referred to as pSica series, and the plasmids were respectively designated as pSica-1 to pSica-5 in accordance with the different partition sites.

The luminescence values of the respective probes were compared, and the luminescence values of the probes having partition sites #1 to #3 were shown to be almost zero, while the luminescence values of the probes having partition sites #4 and #5 exhibited luminescence values as high as about 5,000,000 RLU (FIG. 3). These results suggest that the seven amino acid residues present between the partition sites #3 and #4 could be the active center of GLuc. It is also shown from the results of FIG. 3 and FIG. 4 that the region between the partition sites #4 and #5 corresponds to the optimal partition site for producing a single-molecule-format luminescent probe utilizing GLuc. These results show that since a probe having GLuc fragments dissected at a position near partition sites #4 and #5, can restore sufficient luminescent enzyme activity, the probe is highly excellent as a probe for analysis (real-time luminescent probe) which senses the increase or decrease of the calcium ion concentration as an index. At the same time, since a possibility was suggested such that the amino acid residues present between the partition site #3, which resulted in almost no light emission, and the partition site #4, which resulted in intense light emission, could include an important amino acid sequence responsible for the luminescence activity of the enzyme, the following point mutation experiment was performed (Example 3).

Meanwhile, the probe produced as control using the FLuc fragments, did not exhibit sensitivity to calcium (FIG. 2(B)).

Example 3

Production of Point-mutated Type Probes and Determination of Luminescence Spectrum Thereof There exists a sequence of seven amino acid residues (93RCHTYEG99) between the dissection sites #3 and #4 of GLuc. In this experiment, N-terminal fragments each having a single point-mutated to glycine (G), were produced in order to search, among those seven amino acid residues, for the amino acid which is responsible for the luminescence activity of GLuc. Thus, six kinds of plasmids were produced using the nucleic acids which respectively encode the fusion proteins comprising a single point-mutated amino acid in the GLuc-N-terminal fragments.

To produce these point mutants, the following procedure was conducted. PCR-based synthesis of a cDNA encoding RCHTYEG, which is a portion of the amino acid sequence of the N-terminal fragment of GLuc, was carried out using pSica-4 as a template, and primer systems which generate the respective point mutations. The mutated N-terminal fragments thus synthesized were purified, and the two termini of each fragment were digested with HindIII and KpnI restriction enzymes. Another pSica-4 was also digested at the HindIII and KpnI sites in the same manner, and plasmids respectively incorporated with the mutated type N-terminal fragments were subcloned. These plasmids were respectively renumbered and designated as pSica-4 m1 to pSica-4 m6. The term "m" as used herein means mutation.

The luminescence spectra of cells which were transfected respectively with the plasmids pSica-4 m1 to pSica-4 m6, were measured (FIG. 4). It was found from the results that the luminescence spectrum of pSica-4 m6 had a higher luminescence value near 480 nm, as compared with other cases. Meanwhile, the luminescence value near 480 nm as given by the pSica-4 m4 corresponded to the median of the luminescence values given by pSica-4 m6 and the other plasmids. It was also found that the luminescence values given by pSica-4 m1 to pSica-4 m3 and pSica-4 m5 were relatively low. These results can be interpreted as follows.

It was understood that in the sequence of seven amino acid residues (RCHTYEG) present between the dissection sites #3 and #4 of Gluc, the amino acids important for luminescence activity were R, C, H and Y, and compared to these, the amino acid residue T at position 96 and the amino acid residue E at position 98 in the amino acid sequence of GLuc were not very important. This experiment shows that the single-molecule-format real-time luminescent probe of the present invention not only provides a means for quantitative visualization of stimulators, but also provides a promising means for the field of basic research on luminescent proteins themselves.

Example 4

Measurement of ATP Concentration-dependent Luminescence Change in COS-7 Cells Carrying pSica-5 pSica-5 was transfected into COS-7 cells which have been cultured on a 24-well plate, using a transfection reagent (TransIT-LT1 (Mirus)). Then, the cells were cultured for 16 hours, and then the culture medium was exchanged with 200 µL of a mixed solution of a HBSS buffer (containing 1.3 mM $Ca^{2+}$) and the substrate. The values of luminescence change obtained thereafter were monitored by a luminescent plate reader (FIG. 5). After about 5 minutes, ATP was added at different concentrations, and changes in the luminescence values obtained thereafter were monitored. According to the results, stimulant dose-dependent changes in the luminescence values were observed with 1 mM, 100 µM and 10 µM ATP stimulations. Meanwhile, no detectable change was recognized in the luminescence values for the buffer solution itself (phosphate buffer saline; PBS).

Example 5

Measurement of Luminescence Intensity Variances Due to External Stimulators in COS-7 Cells Transfected with pSica-5 pSica-5 was transfected into COS-7 cells which have been cultured on a 24-Well Plate, using a transfection reagent (TransIT-LT1 (Mirus)). Then, the cells were cultured for 16 hours, and then the medium was exchanged with 200 µL of a mixed solution of a HBSS buffer solution (containing 1.3 mM $Ca^{2+}$) and a substrate. The luminescence variances obtained thereafter were monitored by a luminescent plate reader (FIG. 6). Under the conditions established such that exogenous $Ca^{2+}$ would enter into the cells by adding 2 µM ionomycin, the luminescence variances were monitored (introduction of exogenous $Ca^{2+}$ into the cells). Furthermore, under the conditions established such that influx of $Ca^{2+}$ from the endoplasmic reticulum (ER) in the cells to the cytoplasm was promoted by adding 1 mM ATP and 1 mM histamine, the fluctuation in the luminescence values was measured (promotion of $Ca^{2+}$ secretion inside the cells). The changes in the luminescence values were monitored with a luminescence plate reader throughout the entire process. From these results, it was understood that the concentration variances of $Ca^{2+}$, which is a representative means for signal transduction in the cells, can be measured in intact living cells, on a real-time basis.

Example 6

Ca²⁺ Concentration-dependent Luminescence Intensity in Living Cells Transfected with pSica-5 and Dose-response Curves pSica-5 was transfected into COS-7 cells or HeLa cells which have been cultured on a 24-well plate, using a transfection reagent (TransIT-LT1 (Mirus)). Then, the cells were cultured for 16 hours, and then the cell culture medium was exchanged with 200 μL of a PBS buffer solution supplemented with coeleterazine, which is the specific substrate, and 2 μM ionomycin. The values of luminescence change obtained thereafter were monitored by a luminescent plate reader (Mithras LB940; Berthold) (FIG. 7(A)). Four minutes after stabilization of the background luminescence, Ca²⁺ was added to the cells on the wells at concentrations ranging from $10^{-3.5}$ M to $10^{-5.5}$ M. Thereafter, the changes in the luminescence values were immediately monitored by the above-mentioned luminescence plate reader. Changes in the luminescence values, which were dependent on the concentration of added Ca²⁺, were monitored. Based on the values of luminescence fluctuations in this Ca²⁺ concentration range, three kinds of calibration curves were produced with respect to the Ca²⁺ concentration in the cultured cells.

It was found that the 50% effective concentrations ($EC_{50}$) obtained based on the changes in the luminescence intensities due to the Ca²⁺ concentration, were $0.25 \times 10^{-4}$ M and $0.50 \times 10^{-4}$ M for the COS-7 cells and the HeLa cells, respectively. The dissociation coefficient (Kd) between CaM and Ca²⁺ induced in the HeLa cells was found to be $0.63 \times 10^{-17}$ M⁴, from the luminescence values.

Variances in the luminescence intensity induced by the ATP concentration in COS-7, MCF-7 and HeLa cells, which had been respectively transfected with pSica-5, were measured (FIG. 7(B)). When stimulated by ATP, the ATP receptors present on the cell membrane recognized ATP, the activated receptors immediately elevate IP3 levels. As a result, Ca²⁺ concentration is increased under the action of IP3. Accordingly, there was manifested luminescence intensity which is dependent on the concentration of externally supplemented ATP. The intracellular Ca²⁺ levels increased by the stimulation of 1 mM ATP in the respective cells are presented in the following table.

TABLE 2

Ca²⁺ concentration values increased by ATP stimulation in living cells

| Stimulant | Stimulant concentration | Host cell | Measured average of Ca²⁺ concentrations (ave) | Measured standard error of Ca²⁺ concentrations (SD) |
|---|---|---|---|---|
| ATP | 1 mM | MCF-7 | $1.30 \times 10^{-5}$ M | $0.97 \times 10^{-5}$ M |
| ATP | 1 mM | COS-7 | $3.74 \times 10^{-5}$ M | $3.55 \times 10^{-5}$ M |

Example 7

Measurement of Changes in Luminescence Intensity Due to External Stimulator in COS-7 Cells Transfected with pSicam pSicam was transfected into COS-7 cells which had been cultured on a 12-well plate. After 16 hours, the external stimulus-dependent changes in the luminescence intensity were monitored by a luminescence plate reader (FIG. 8). In regard to FIG. 8(A), the cell culture medium on the 12-well plate was exchanged with 200 μL of a mixed solution of a HBSS buffer solution (containing 1.3 mM Ca²⁺) and the substrate, and the luminescence variances obtained thereafter were monitored by a luminescence plate reader. Then, the changes in the luminescence values were monitored under the conditions of the presence or the absence of ATP. In regard to FIG. 8(B), first, the cell culture medium on the 12-well plate was exchanged with 200 μL of a mixed solution of a HBSS buffer solution (containing 1.3 mM Ca²⁺) and the substrate, and the luminescence variances obtained thereafter were monitored by a luminescence plate reader for about 5 minutes. Then, 2 μL of ionomycin was added, and finally the system was stimulated with 1 mM ATP. The changes in the luminescence intensity over the various steps were continuously monitored by a luminescence plate reader. These results showed that COS-7 cells transfected with pSicam enhanced the luminescence intensity in an external stimulus-dependent manner. The reason for such results can be interpreted such that the binding between the M13-fused CaM inserted into pSicam occurred in an external stimulus-dependent manner, and as a result, the interaction between the GLuc fragments linked to the outer sides of CaM and M13 caused restoration of the enzyme activity. FIG. 8(C) is a conceptual diagram depicting the restoration of enzyme activity triggered by the binding between CaM and M13, and the right-hand side shows the liquid crystal structure of when CaM binds with M13 under the condition of the presence of calcium.

These experimental results show that the present technique is capable of monitoring the molecular dynamics occurring inside and outside living cells on a real-time basis.

Example 8

Construction of Plasmid for Single-molecule-format Luminescent Probe Incorporated with Nuclear Receptor, and Measurement of the Stimulator Sensitivity To examine whether the optimum dissection sites within GLuc, which have been discovered by the experiments in this invention using the above-mentioned plasmids, are generally applicable, a plasmid carrying a nuclear receptor (NR) was constructed.

cDNAs encoding the ligand binding domains (LBD) of a human-derived male sex hormone receptor (human androgen receptor; AR GenBank/M27430) or glucocorticoid receptor (human glucocorticoid receptor; GR GenBank/P04150), which are representative nuclear receptors, were provided, and the N-terminus and C-terminus thereof were each incorporated with restriction enzyme sites KpnI and BamHI by PCR reaction. Plasmids were subcloned in which cDNA of CaM was replaced with the ARLBD or GRLBD in the backbone of the above-described pSica-5, in place of the. These plasmids were designated as pSimar and pSimgr, respectively. FIG. 9(A) is a gene design diagram of the constructs in pSimar and pSimgr.

FIGS. 9(B) and 9(C) show the ligand sensitivity of the living cells transfected with pSimar and psimgr, respectively. The cells transfected with pSimar enhanced the luminescence intensity in specific to the male sex hormone (DHT), while the cells transfected with pSimgr exhibited strong sensitivity only to a stress hormone (cortisol). These results indicate that the probes mounted with these AR LBD and GR LBD are definitely expressed in the living cells, and that the probes have agonist selectivity and sensitivity. Furthermore, since the GLuc fragments fused in these probes coincide with the dissection site employed by the pSica-5, it is strongly suggested that this dissection site can be generally useful for various types of single-molecule-format luminescence imaging probes.

TABLE 3

Amino acid sequences used in this Example

| Name | Amino acid sequence | SEQ ID NO. |
|---|---|---|
| M13, which is a myosin light chain kinase-derived peptide | KRRWKKNFIAVSAANRFKKISSSGAL | 1 |
| Leucine-rich peptide found within AR NTD region, which was linked to AR LBD | $^{50}$PGASLLLLQQ$^{59}$ | 2 |
| LXXLL motive (GenBank Accession number: AB219976) found within Nuclear receptor Interaction Domain 3 (NID3) of mouse-derived GRIP1, which was linked to GR LBD | $^{742}$NALLRYLLDKD$^{752}$ | 3 |
| N-terminal fragment of GLuc partitioned at the optimum dissection site | $^{1}$MKPTENNEDFNIVAVASNFATTDLD ADRGKLPGKKLPLEVLKEMEANARK AGCTRGCLICLSHIKCTPKMKKFIP GRCHTYEGDKESAQG$^{106}$ | 4 |
| C-terminal fragment of GLuc partitioned at the optimum dissection site | $^{107}$GIGEAIVDIPEIPGFKDLEPMEQ FIAQVDLCVDCTTGCLKGLANVQCSD LLKKWLPQRCATFASKIQGQVDKIKG AGGD$^{185}$ | 5 |

Example 9

Visualization of Ca$^{2+}$ Activity using Luminescent Paper Strip

Since the single-molecule-format real-time luminescent probe of the present invention is formed such that all the elements necessary for signal recognition and light (luminescence) emission are integrated in a single molecule, the probe can be widely used in living cells as well as in vitro experiments. As an example, a means for visualization of a ligand can be provided, in the form of a paper strip mounted on a glass plate.

In the present Example, a cross-shaped strip was cut out from a nitrocellulose paper, and the cut paper strip was attached to a glass plate to construct a luminescent strip (FIG. 10). The probe separated and purified from the living cells was dripped and dried at the ends of the cross-shaped luminescent strip, and then the sensitivity to Ca$^{2+}$ was measured. It was found that under the conditions of the presence of Ca$^{2+}$ ions, strong luminescence was displayed. On the other hand, it was found that under the conditions of the absence of Ca$^{2+}$ ions, luminescence was as weak as to be indiscernible.

These results indicate that this single-molecule-format real-time luminescent probe can be useful not only in real-time luminescence imaging in living cells, but also in constructing general analysis tools for cell-free systems.

INDUSTRIAL APPLICABILITY

The present invention relates to visualization of molecular phenomena which occur under direct influence of the cell membrane receptors, using the fundamental mechanism of the sensory organs (having receptors on the cell membrane) of the human body, and provides a basic biological analysis method which has good sensitivity and can be applied in a wide range of fields, while making using of the principle of signal amplification in organisms per se. When the probe of the present invention is introduced into living cells, the cells themselves are converted to sensor cells, and allow visualization imaging of various life phenomena in living cells on a real-time basis. For instance, in regard to the histamine which is induced by food poisoning or allergy, the fluctuation in Ca$^{2+}$ levels which increases in living cells can be measured. In addition to that, application can also be made in the same manner, to the visual sense, auditory sense, tactile sense, energy metabolism and the like.

Furthermore, a miniaturized analytical means which operates on-site and on a real-time basis, is also provided for cell-free systems, by dripping and drying the probe of the present invention on one side of a paper strip, and then dropping a small amount of a sample thereon at the time of measurement. A simple analytical means which enables quantitative visualization of a target ligand, can be provided in the same form as commercially available pregnancy diagnosis reagents or ovulation diagnosis reagents.

The present invention is helpful in high-speed screening of intracellular factors of disorder, such as stress substances, and in quantitative evaluation of the drug efficacy of anticancer agents with a rapid, simple, and high sample throughput (development of new drugs).

The invention claimed is:

1. A single-chain fusion protein comprising:
   an N-terminal fragment and a C-terminal fragment of Gaussia luciferase, each of the N-terminal fragment and the C-terminal fragment being generated by partitioning Gaussia luciferase at position 106 in the entire amino acid sequence thereof; and
   a second messenger-recognition protein, the N- and C-termini of which are respectively linked to the N-terminal fragment and the C-terminal fragment of partitioned Gaussia luciferase, and
   wherein the single-chain fusion protein is capable of a conformational change of the second messenger-recognition protein by binding or unbinding a second messenger, thereby causing the association or dissociation between the N-terminal fragment and the C-terminal fragment.

2. The single-chain fusion protein according to claim 1 wherein the single-chain fusion protein further comprises a peptide which is capable of reversibly binding the second messenger-recognition protein and the single-chain fusion protein is capable of the conformational change of the second messenger-recognition protein by the binding or unbinding a second messenger, followed by binding of the conformation-changed second messenger-recognition protein to the peptide.

3. The single-chain fusion protein according to claim 1, wherein the second messenger is $Ca^{2+}$ ion, and the second messenger-recognition protein is calmodulin.

4. The single-chain fusion protein according to claim 2, wherein the peptide which is capable of reversibly binding calmodulin which recognizes $Ca^{2+}$ ion, is M13 peptide, and the single-chain fusion protein is capable of the conformational change of calmodulin by its binding $Ca^{2+}$ ions, followed by an interaction of the conformation-changed calmodulin with the M13 peptide, thereby causing the subsequent association or dissociation between the fragments of Gaussia luciferase.

5. A tandem nucleic acid molecule comprising:
   a cDNA encoding a single-chain fusion protein comprising:
      an N-terminal fragment and a C-terminal fragment of Gaussia luciferase, each of the N-terminal fragment and the C-terminal fragment being generated by partitioning Gaussia luciferase at position 106 in the entire amino acid sequence thereof; and
      a second-messenger protein, the N- and C-termini of which are respectively linked to the N-terminal fragment and the C-terminal fragment of partitioned Gaussia luciferase, and
      wherein the single-chain fusion protein is capable of a conformational change of the second messenger-recognition protein by binding or unbinding a second messenger, thereby causing the association or dissociation between the N-terminal fragment and the C-terminal fragment.

6. The tandem nucleic acid molecule according to claim 5, further comprising, in the nucleic acid molecule, an oligomer encoding a peptide which is capable of reversibly binding the second messenger-recognition protein.

7. An expression vector comprising the nucleic acid molecule according to claim 5, the expression vector being capable of expressing a single-chain fusion protein comprising:
   an N-terminal fragment and a C-terminal fragment of Gaussia luciferase, each of the N-terminal fragment and the C-terminal fragment being generated by partitioning Gaussia luciferase position 106 in the entire amino acid sequence thereof; and
   a second messenger-recognition protein, the N- and C-termini of which are respectively linked to the N-terminal fragment and the C-terminal fragment of partitioned Gaussia luciferase, and
   wherein the single-chain fusion protein is capable of a conformational change of the second messenger-recognition protein by binding or unbinding a second messenger, thereby causing the association or dissociation between the N-terminal fragment and the C-terminal fragment.

8. An isolated transformed cell by transfection of the expression vector according to claim 7, the transformed cell expressing a single-chain fusion protein comprising:
   an N-terminal fragment and a C-terminal fragment of Gaussia luciferase, each of the N-terminal fragment and the C-terminal fragment being generated by partitioning Gaussia luciferase at position 106 in the entire amino acid sequence thereof; and
   a second messenger-recognition protein, the N- and C-termini of which are respectively linked to the N-terminal fragment and the C-terminal fragment of partitioned Gaussia luciferase, and
   wherein the single-chain fusion protein is capable of a conformational change of the second messenger-recognition protein by binding or unbinding a second messenger, thereby causing the association or between the N-terminal fragment and the C-terminal fragment.

9. An analytical reagent or a kit comprising the analytical reagent, for detecting, identifying or quantifying a ligand which stimulates a cell surface receptor, wherein the analytical reagent includes the single-chain fusion protein according to claim 1, as an active ingredient.

10. An analytical reagent or a kit comprising the analytical reagent comprising transformed cells according to claim 8, wherein the single chain fusion protein is expressed within the cell.

11. The analytical kit according to claim 10, wherein the analytical reagent is immobilized on at least a part of a paper piece, a fiber segment, a microtiter plate or a probe element.

12. An analytical reagent or a kit comprising the analytical reagent, for detecting, identifying or quantifying a ligand which stimulates a surface receptor of a living cell, wherein the analytical reagent includes the expression vector according to claim 7 as an active ingredient, and the analytical reagent is transfected into a living cell and expressed within the living cell to visualize the dynamics of a second messenger.

13. A method for detecting, identifying or quantifying a second messenger, the method comprising:
   transfecting the expression vector according to claim 7 into cells to express the single chain fusion protein within the cells, and
   observing an increase or decrease of a light emitted from the single chain fusion protein.

14. The method for detecting, identifying or quantifying a second-messenger according to claim 13, wherein the expression vector is capable of expressing the single-chain fusion protein further comprising a peptide which is capable of reversibly binding the second messenger-recognition protein, and
   wherein the conformational change of the second messenger-recognition protein is induced by the binding or unbinding a second messenger, followed by interaction of the second messenger-recognition protein to a peptide which is capable of binding reversibly the second messenger-recognition protein.

15. A method for detecting, identifying or quantifying a ligand which stimulates a cell surface receptor, the method comprising:
   transfecting the expression vector according to claim 7 into cells to express a single chain fusion protein within the cells,
   observing the increase and decrease of a light emission from the single chain fusion protein, thereby analyzing the dynamics of the second messenger in the cells.

16. The method for detecting, identifying or quantifying a ligand which stimulates a cell surface receptor according to claim 15, wherein the conformational change of the second messenger-recognition protein is induced by the binding or unbinding a second messenger, followed by interaction of the second messenger-recognition protein with a peptide is capable of binding reversibly the second messenger-recognition protein.

17. A method comprising:
   detecting, identifying or quantifying a free calcium concentration in a physiological or environmental sample by the method according to claim 13.

18. The single-chain fusion protein according to claim 1, wherein the N-terminal fragment is a polypeptide comprising the amino acid sequence set forth in SEQ ID NO. 4, and the C-terminal fragment is a polypeptide comprising the amino acid sequence set forth in SEQ ID NO. 5.

19. An analytical reagent or a kit comprising the analytical reagent, for detecting, identifying or quantifying a second messenger, wherein the analytical reagent includes the single-chain fusion protein according to claim 18, as an active ingredient.

20. The tandem nucleic acid molecule according to claim 5, wherein the N-terminal fragment comprises the amino acid sequence of SEQ ID NO.4, and wherein the C-terminal fragment comprises the amino acid sequence. of SEQ ID NO.5.

21. The tandem nucleic acid molecule according to claim 5, wherein the second messenger-recognition protein is selected from the group consisting of a $Ca^{2+}$ recognition protein, a cAMP-recognition protein, a diacylglycerol-recognition protein, and a cGMP-recognition protein.

22. The tandem nucleic acid molecule according to claim 5, wherein the second messenger-recognition protein is calmodulin.

* * * * *

SEQUENCE LISTING

<160> NUMBER OF SEQ ID NOS: 5

<210> SEQ ID NO 1
<211> LENGTH: 26
<212> TYPE: PRT
<213> ORGANISM: Artificial
<220> FEATURE:
<223> OTHER INFORMATION: Myosin light chain kinase

<400> SEQUENCE: 1

Lys Arg Arg Trp Lys Lys Asn Phe Ile Ala Val Ser Ala Ala Asn Arg
1               5                   10                  15

```
Phe Lys Lys Ile Ser Ser Ser Gly Ala Leu
            20                  25
```

<210> SEQ ID NO 2
<211> LENGTH: 10
<212> TYPE: PRT
<213> ORGANISM: Artificial
<220> FEATURE:
<223> OTHER INFORMATION: Leucine-rich peptide

<400> SEQUENCE: 2

```
Pro Gly Ala Ser Leu Leu Leu Gln Gln
1               5                   10
```

<210> SEQ ID NO 3
<211> LENGTH: 11
<212> TYPE: PRT
<213> ORGANISM: Artificial
<220> FEATURE:
<223> OTHER INFORMATION: LXXLL(NID3)

<400> SEQUENCE: 3

```
Asn Ala Leu Leu Arg Tyr Leu Leu Asp Lys Asp
1               5                   10
```

<210> SEQ ID NO 4
<211> LENGTH: 90
<212> TYPE: PRT
<213> ORGANISM: Artificial
<220> FEATURE:
<223> OTHER INFORMATION: N-GLuc

<400> SEQUENCE: 4

```
Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Met Glu Ala Asn Ala
        35                  40                  45

Arg Lys Ala Gly Cys Thr Arg Gly Cys Leu Ile Cys Leu Ser His Ile
    50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly
                85                  90
```

<210> SEQ ID NO 5
<211> LENGTH: 79
<212> TYPE: PRT
<213> ORGANISM: Artificial
<220> FEATURE:
<223> OTHER INFORMATION: C-GLuc

<400> SEQUENCE: 5

```
Gly Ile Gly Glu Ala Ile Val Asp Ile Pro Glu Ile Pro Gly Phe Lys
1               5                   10                  15

Asp Leu Glu Pro Met Glu Gln Phe Ile Ala Gln Val Asp Leu Cys Val
            20                  25                  30

Asp Cys Thr Thr Gly Cys Leu Lys Gly Leu Ala Asn Val Gln Cys Ser
        35                  40                  45

Asp Leu Leu Lys Lys Trp Leu Pro Gln Arg Cys Ala Thr Phe Ala Ser
    50                  55                  60
```

-continued

```
Lys Ile Gln Gly Gln Val Asp Lys Ile Lys Gly Ala Gly Gly Asp
 65                  70                  75
```